US008652527B1

(12) United States Patent
Betterman et al.

(10) Patent No.: US 8,652,527 B1
(45) Date of Patent: Feb. 18, 2014

(54) EXTENDED-RELEASE TOPIRAMATE CAPSULES

(71) Applicants: Sarah Michelle Betterman, Champlin, MN (US); Jaidev Srinvas Tantry, Maple Grove, MN (US); Laura Marie Patrick, Eden Prairie, MN (US)

(72) Inventors: Sarah Michelle Betterman, Champlin, MN (US); Jaidev Srinvas Tantry, Maple Grove, MN (US); Laura Marie Patrick, Eden Prairie, MN (US)

(73) Assignee: Upsher-Smith Laboratories, Inc, Maple Grove, MN (US)

( * ) Notice: Subject to any disclaimer, the term of this patent is extended or adjusted under 35 U.S.C. 154(b) by 0 days.

(21) Appl. No.: 13/847,042

(22) Filed: Mar. 19, 2013

Related U.S. Application Data

(60) Provisional application No. 61/779,576, filed on Mar. 13, 2013, provisional application No. 61/788,880, filed on Mar. 15, 2013.

(51) Int. Cl.
*A61K 9/16* (2006.01)
*A61K 9/28* (2006.01)
*C07D 311/02* (2006.01)
*C07D 493/12* (2006.01)

(52) U.S. Cl.
CPC ... *A61K 9/16* (2013.01); *A61K 9/28* (2013.01); *A61K 9/2866* (2013.01); *A61K 2201/15* (2013.01); *C07D 311/02* (2013.01); *C07D 493/12* (2013.01); *Y10S 514/963* (2013.01); *Y10S 514/964* (2013.01)
USPC ........... 424/489; 424/457; 424/462; 424/474; 514/963; 514/964; 549/387

(58) Field of Classification Search
None
See application file for complete search history.

(56) References Cited

U.S. PATENT DOCUMENTS

| | | | |
|---|---|---|---|
| 4,513,006 A | 4/1985 | Maryanoff et al. |
| 5,753,693 A | 5/1998 | Shank |
| 5,753,694 A | 5/1998 | Shank |
| 5,760,006 A | 6/1998 | Shank et al. |
| 5,760,007 A | 6/1998 | Shank et al. |
| 5,935,933 A | 8/1999 | Shank et al. |
| 5,952,187 A | 9/1999 | Stenglein et al. |
| 5,998,380 A | 12/1999 | Ehrenberg et al. |
| 6,071,537 A | 6/2000 | Shank |
| 6,191,117 B1 | 2/2001 | Kozachuk |
| 6,191,163 B1 | 2/2001 | Cottrell |
| 6,201,010 B1 | 3/2001 | Cottrell |
| 6,214,867 B1 | 4/2001 | Connor |
| 6,319,903 B1 | 11/2001 | Carrazana et al. |
| 6,323,236 B2 | 11/2001 | McElroy |
| 6,340,475 B2 | 1/2002 | Shell et al. |
| 6,362,220 B1 | 3/2002 | Cottrell |
| 6,395,767 B2 | 5/2002 | Robl et al. |
| 6,395,783 B1 | 5/2002 | Dewey et al. |
| 6,414,126 B1 | 7/2002 | Ellsworth et al. |
| 6,420,369 B1 | 7/2002 | Marcotte |
| 6,472,370 B1 | 10/2002 | VanKammem |
| 6,479,467 B1 | 11/2002 | Buchanan et al. |
| 6,486,198 B1 | 11/2002 | Berlant |
| 6,503,884 B1 | 1/2003 | Ehrenberg et al. |
| 6,515,117 B2 | 2/2003 | Ellsworth et al. |
| 6,541,520 B1 | 4/2003 | Dewey et al. |
| 6,544,998 B2 | 4/2003 | Mylari |
| 6,548,529 B1 | 4/2003 | Robl et al. |
| 6,552,000 B2 | 4/2003 | VanKammem |
| 6,555,519 B2 | 4/2003 | Washburn |
| 6,559,293 B1 | 5/2003 | Almarsson et al. |
| 6,562,865 B1 | 5/2003 | Codd et al. |
| 6,620,819 B2 | 9/2003 | Marcotte |
| 6,622,036 B1 | 9/2003 | Suffin |
| 6,627,653 B2 | 9/2003 | Plata et al. |
| 6,635,280 B2 | 10/2003 | Shell et al. |
| 6,673,815 B2 | 1/2004 | Devasthale et al. |
| 6,683,056 B2 | 1/2004 | Washburn et al. |
| 6,686,337 B2 | 2/2004 | Connor |
| 6,696,091 B2 | 2/2004 | Thakur et al. |
| 6,699,840 B2 | 3/2004 | Almarsson et al. |
| 6,720,348 B2 | 4/2004 | Mylari |
| 6,774,112 B2 | 8/2004 | Gougoutas |
| 6,797,692 B1 | 9/2004 | Ikonomidou |
| 6,875,782 B2 | 4/2005 | Cheng et al. |
| 6,890,951 B2 | 5/2005 | Dewey et al. |
| 6,893,661 B1 | 5/2005 | Odidi et al. |

(Continued)

FOREIGN PATENT DOCUMENTS

EP   1 336 602 A1   8/2003
EP   1 548 024 A1   6/2005
(Continued)

OTHER PUBLICATIONS

MA Frohoff-Hulsmann, A Schmitz, BC Lippold. "Aqueous ethyl cellulose dispersions containing plasticizers of different water solubility and hydroxypropyl methylcellulose as coating material for diffusion pellets I. Drug release rates from coated pellets." International Journal of Pharmaceutics, vol. 177, 1999, pp. 69-82.*
MM Al-Tabakha. "HPMC Capsules: Current Status and Future Prospects." Journal of Pharmacy and Pharmaceutical Sciences, vol. 13(3), 2010, pp. 428-442.*
U.S. Appl. No. 60/841,924, filed Aug. 31, 2006, Nangia et al.
Bialer et al., "Pharmacokinetic interactions of topiramate," 2004 *Clin Pharmacokinet*. 43:763-80.
Bialer, "Extended-release formulations for the treatment of epilepsy" Sep. 18, 2007, *CNS Drugs* 21(9):765-74.
Bourgeois, "Important pharmacokinetic properties of antiepileptic drugs," 1995 *Epilepsia* 36(Suppl 5):S1-7.

(Continued)

*Primary Examiner* — Frederick Krass
*Assistant Examiner* — Isaac Shomer
(74) *Attorney, Agent, or Firm* — Mueting, Raasch & Gebhardt, P.A.

(57) ABSTRACT

An extended-release topiramate capsule that includes a capsule shell containing a single population of coated particles; wherein each coated particle includes a core and a coating thereon; wherein each particle core includes a homogeneous mixture comprising topiramate throughout its core; and wherein the coating includes one or more release controlling agent(s).

30 Claims, No Drawings

(56) References Cited

U.S. PATENT DOCUMENTS

| | | |
|---|---|---|
| 6,906,099 B2 | 6/2005 | Dewey et al. |
| 6,908,902 B2 | 6/2005 | Plata et al. |
| 6,921,775 B2 | 7/2005 | Jensen et al. |
| 6,936,590 B2 | 8/2005 | Washburn et al. |
| 6,949,518 B1 | 9/2005 | Chu et al. |
| 6,951,844 B2 | 10/2005 | Hangeland |
| 6,967,212 B2 | 11/2005 | Cheng et al. |
| 6,995,180 B2 | 2/2006 | Magnin et al. |
| 7,018,983 B2 | 3/2006 | Ehrenberg et al. |
| 7,041,650 B2 | 5/2006 | Abdel Magid et al. |
| 7,053,106 B2 | 5/2006 | Cheng et al. |
| 7,056,890 B2 | 6/2006 | Najarian |
| 7,078,526 B2 | 7/2006 | Remenar et al. |
| 7,098,188 B2 | 8/2006 | Abdel Magid et al. |
| 7,109,174 B2 | 9/2006 | Plata-Salaman et al. |
| 7,125,560 B2 | 10/2006 | Thakur et al. |
| 7,196,209 B2 | 3/2007 | Adkins et al. |
| 7,208,477 B2 | 4/2007 | Shapira et al. |
| 7,238,470 B2 | 7/2007 | Hebebrand et al. |
| 7,253,283 B2 | 8/2007 | Weinstein et al. |
| 7,273,881 B2 | 9/2007 | Yang |
| 7,279,485 B2 | 10/2007 | Cheng et al. |
| 7,317,024 B2 | 1/2008 | Yang |
| 7,351,695 B2 | 4/2008 | Almarssoo et al. |
| 7,446,107 B2 | 11/2008 | Remenar et al. |
| 7,498,311 B2 | 3/2009 | Ehrenberg et al. |
| 7,553,818 B2 | 6/2009 | Najarian |
| 7,611,728 B2 | 11/2009 | Kidane et al. |
| RE41,148 E | 2/2010 | Burnside et al. |
| 7,659,256 B2 | 2/2010 | Najarian |
| 7,674,776 B2 | 3/2010 | Najarian |
| 7,838,498 B2 | 11/2010 | Chen et al. |
| 7,838,499 B2 | 11/2010 | Chen et al. |
| 7,858,122 B2 | 12/2010 | Kshirsagar et al. |
| 7,884,113 B2 | 2/2011 | Sun et al. |
| 7,897,636 B2 | 3/2011 | Breslav et al. |
| 7,927,613 B2 | 4/2011 | Almarsson et al. |
| 7,947,733 B2 | 5/2011 | Robbins et al. |
| 8,101,592 B2 | 1/2012 | Xie et al. |
| 8,106,021 B2 | 1/2012 | Chen et al. |
| 8,119,621 B2 | 2/2012 | Liotta et al. |
| 8,119,808 B2 | 2/2012 | Sun et al. |
| 8,160,720 B2 | 4/2012 | Wingeier et al. |
| 8,190,270 B2 | 5/2012 | Wingeier et al. |
| 8,298,580 B2 | 10/2012 | Liang et al. |
| 2002/0082252 A1 | 6/2002 | Hochman |
| 2002/0169103 A1 | 11/2002 | Dewey et al. |
| 2003/0004176 A1 | 1/2003 | Dewey et al. |
| 2003/0032661 A1 | 2/2003 | Croenlein |
| 2003/0051728 A1 | 3/2003 | Lloyd et al. |
| 2003/0072802 A1 | 4/2003 | Cutler et al. |
| 2003/0091630 A1 | 5/2003 | Louie-Helm et al. |
| 2003/0133951 A1 | 7/2003 | Coe et al. |
| 2003/0133985 A1 | 7/2003 | Louie-Helm et al. |
| 2003/0139332 A1 | 7/2003 | Noble et al. |
| 2003/0203055 A1 | 10/2003 | Rao et al. |
| 2003/0235576 A1 | 12/2003 | Duettmann et al. |
| 2004/0082519 A1 | 4/2004 | Hedner et al. |
| 2004/0082543 A1 | 4/2004 | Cheung |
| 2004/0087513 A1 | 5/2004 | Duettmann et al. |
| 2004/0104501 A1 | 6/2004 | Petereit et al. |
| 2004/0110733 A1 | 6/2004 | Borlak et al. |
| 2004/0115262 A1 | 6/2004 | Jao et al. |
| 2004/0122033 A1 | 6/2004 | Nargund et al. |
| 2004/0142938 A1 | 7/2004 | Sher et al. |
| 2004/0204472 A1 | 10/2004 | Briggs et al. |
| 2004/0229943 A1 | 11/2004 | Hughes et al. |
| 2004/0258758 A1 | 12/2004 | Gustow et al. |
| 2005/0031544 A1 | 2/2005 | Njemanze |
| 2005/0058707 A1 | 3/2005 | Reyes et al. |
| 2005/0070524 A1 | 3/2005 | Stephenson et al. |
| 2005/0095579 A1 | 5/2005 | Thiruvengadam et al. |
| 2005/0119312 A1 | 6/2005 | Cheng et al. |
| 2005/0124533 A1 | 6/2005 | Schatzberg et al. |
| 2005/0129765 A1 | 6/2005 | Li et al. |
| 2005/0136106 A1 | 6/2005 | Sandler |
| 2005/0136108 A1 | 6/2005 | Yam et al. |
| 2005/0169992 A1 | 8/2005 | Jao et al. |
| 2005/0181071 A1 | 8/2005 | Binder |
| 2005/0182049 A1 | 8/2005 | Howard |
| 2005/0182105 A1 | 8/2005 | Nirschl et al. |
| 2005/0203287 A1 | 9/2005 | Batchu et al. |
| 2005/0239839 A1 | 10/2005 | Hamann et al. |
| 2005/0287213 A1 | 12/2005 | Wong et al. |
| 2006/0034927 A1 | 2/2006 | Casadevall et al. |
| 2006/0035914 A1 | 2/2006 | Hochman |
| 2006/0039866 A1 | 2/2006 | Rao et al. |
| 2006/0039867 A1 | 2/2006 | Rao et al. |
| 2006/0058224 A1 | 3/2006 | Yancopoulos et al. |
| 2006/0063722 A1 | 3/2006 | Washburn et al. |
| 2006/0121112 A1 | 6/2006 | Jenkins et al. |
| 2006/0128687 A1 | 6/2006 | Sher et al. |
| 2006/0129324 A1 | 6/2006 | Rabinoff et al. |
| 2006/0142576 A1 | 6/2006 | Meng et al. |
| 2006/0148721 A1 | 7/2006 | Erondu |
| 2006/0160776 A1 | 7/2006 | Stephenson et al. |
| 2006/0160834 A1 | 7/2006 | Fong et al. |
| 2006/0166899 A1 | 7/2006 | Teranishi et al. |
| 2006/0173064 A1 | 8/2006 | Lippa et al. |
| 2006/0199796 A1 | 9/2006 | Chen et al. |
| 2006/0204486 A1 | 9/2006 | Pyke et al. |
| 2006/0204578 A1* | 9/2006 | Vergez et al. ............... 424/473 |
| 2006/0211752 A1 | 9/2006 | Kohn et al. |
| 2006/0234950 A1 | 10/2006 | Najarian |
| 2006/0269935 A1 | 11/2006 | Tate et al. |
| 2006/0286163 A1 | 12/2006 | Thakur et al. |
| 2007/0010513 A1 | 1/2007 | Aslanian et al. |
| 2007/0015807 A1 | 1/2007 | Aslanian et al. |
| 2007/0020332 A1 | 1/2007 | Kiel et al. |
| 2007/0026440 A1 | 2/2007 | Broderick et al. |
| 2007/0066644 A1 | 3/2007 | de Lera Ruiz et al. |
| 2007/0066657 A1 | 3/2007 | Tung |
| 2007/0077294 A1 | 4/2007 | Sherman et al. |
| 2007/0099835 A1 | 5/2007 | Qian et al. |
| 2007/0099884 A1 | 5/2007 | Erondu et al. |
| 2007/0099913 A1 | 5/2007 | O'Connor |
| 2007/0111204 A1 | 5/2007 | Delgrosso et al. |
| 2007/0142394 A1 | 6/2007 | Solomon et al. |
| 2007/0167435 A1 | 7/2007 | Mutahi et al. |
| 2007/0173495 A1 | 7/2007 | Palani et al. |
| 2007/0184112 A1 | 8/2007 | Wong et al. |
| 2007/0185056 A1 | 8/2007 | Duan et al. |
| 2007/0185084 A1 | 8/2007 | McKinney et al. |
| 2007/0190043 A1 | 8/2007 | Sych et al. |
| 2007/0191288 A1 | 8/2007 | Shapira et al. |
| 2007/0191289 A1 | 8/2007 | Fushimi et al. |
| 2007/0191371 A1 | 8/2007 | Bennett et al. |
| 2007/0197449 A1 | 8/2007 | Fushimi et al. |
| 2007/0197450 A1 | 8/2007 | Fushimi et al. |
| 2007/0203448 A1 | 8/2007 | Melker et al. |
| 2007/0212428 A1 | 9/2007 | Wittlin |
| 2007/0212685 A1 | 9/2007 | MacDonald et al. |
| 2007/0218139 A1 | 9/2007 | Smith et al. |
| 2007/0224281 A1 | 9/2007 | Park et al. |
| 2007/0232648 A1 | 10/2007 | Dahl et al. |
| 2007/0243254 A1 | 10/2007 | Edgren et al. |
| 2007/0244130 A1 | 10/2007 | Epple et al. |
| 2007/0249583 A1 | 10/2007 | Stein et al. |
| 2007/0258938 A1 | 11/2007 | Roy et al. |
| 2007/0264358 A1 | 11/2007 | Wittlin |
| 2007/0269393 A1 | 11/2007 | Wepfer |
| 2007/0270453 A1 | 11/2007 | Weinstein et al. |
| 2007/0276001 A1 | 11/2007 | Tung |
| 2007/0287713 A1 | 12/2007 | Cheng et al. |
| 2008/0009533 A1 | 1/2008 | Tino et al. |
| 2008/0009534 A1 | 1/2008 | Cheng et al. |
| 2008/0014252 A1 | 1/2008 | DelPrete |
| 2008/0019978 A1 | 1/2008 | Palani et al. |
| 2008/0058370 A1 | 3/2008 | de Lera Ruiz et al. |
| 2008/0064632 A1 | 3/2008 | Amatruda et al. |
| 2008/0078382 A1 | 4/2008 | LeMahieu et al. |
| 2008/0085306 A1 | 4/2008 | Nangia et al. |
| 2008/0118557 A1 | 5/2008 | Liang et al. |
| 2008/0131501 A1 | 6/2008 | Liang et al. |

(56) References Cited

U.S. PATENT DOCUMENTS

| | | |
|---|---|---|
| 2008/0171692 A1 | 7/2008 | Hagmann et al. |
| 2008/0194625 A1 | 8/2008 | Sun et al. |
| 2008/0221161 A1 | 9/2008 | Pinkerton et al. |
| 2008/0226715 A1 | 9/2008 | Cha et al. |
| 2008/0242593 A1 | 10/2008 | Ewing et al. |
| 2008/0242596 A1 | 10/2008 | Chen et al. |
| 2008/0242684 A1 | 10/2008 | Dittrich |
| 2008/0255093 A1 | 10/2008 | Tam et al. |
| 2008/0255194 A1 | 10/2008 | Harbeson |
| 2008/0292700 A1 | 11/2008 | Nghiem et al. |
| 2008/0293777 A1 | 11/2008 | Erlanson et al. |
| 2009/0004254 A1 | 1/2009 | Maibach |
| 2009/0018115 A1 | 1/2009 | Gadde et al. |
| 2009/0048232 A1 | 2/2009 | Ciccocioppo |
| 2009/0048235 A1 | 2/2009 | Xia et al. |
| 2009/0076053 A1 | 3/2009 | Robbins |
| 2009/0098200 A1 | 4/2009 | Temtsin et al. |
| 2009/0099143 A1 | 4/2009 | Lagu et al. |
| 2009/0105124 A1 | 4/2009 | Smith et al. |
| 2009/0117181 A1 * | 5/2009 | Uehara et al. ............ 424/464 |
| 2009/0130216 A1 | 5/2009 | Cartt et al. |
| 2009/0137652 A1 | 5/2009 | Twyman et al. |
| 2009/0157662 A1 | 6/2009 | Suffin et al. |
| 2009/0176865 A1 | 7/2009 | Breslav et al. |
| 2009/0197886 A1 | 8/2009 | Liotta et al. |
| 2009/0232886 A1 | 9/2009 | Sison |
| 2009/0239942 A1 | 9/2009 | Cloyd |
| 2009/0247544 A1 | 10/2009 | Morgan et al. |
| 2009/0258844 A1 | 10/2009 | Hochman |
| 2009/0258902 A1 | 10/2009 | Tung |
| 2009/0270469 A1 | 10/2009 | Gant et al. |
| 2009/0304785 A1 | 12/2009 | Najarian et al. |
| 2009/0304789 A1 | 12/2009 | Najarian et al. |
| 2009/0306051 A1 | 12/2009 | Meyerson et al. |
| 2009/0311347 A1 | 12/2009 | Oronsky et al. |
| 2009/0325961 A1 | 12/2009 | Duan et al. |
| 2010/0056546 A1 | 3/2010 | Gant et al. |
| 2010/0063148 A1 | 3/2010 | Christoph et al. |
| 2010/0069341 A1 | 3/2010 | Liotta et al. |
| 2010/0074973 A1 | 3/2010 | Gant et al. |
| 2010/0076006 A1 | 3/2010 | Johnson et al. |
| 2010/0087422 A1 | 4/2010 | Bird |
| 2010/0105755 A1 | 4/2010 | Gant et al. |
| 2010/0105765 A1 | 4/2010 | Najarian |
| 2010/0113432 A1 | 5/2010 | Gant et al. |
| 2010/0113583 A1 | 5/2010 | Aronne |
| 2010/0119512 A1 | 5/2010 | Feener et al. |
| 2010/0119622 A1 | 5/2010 | Gant et al. |
| 2010/0119624 A1 | 5/2010 | Gant et al. |
| 2010/0120861 A1 | 5/2010 | Gant et al. |
| 2010/0124541 A1 | 5/2010 | Gant et al. |
| 2010/0125085 A1 | 5/2010 | Gant et al. |
| 2010/0129311 A1 | 5/2010 | Gant |
| 2010/0130528 A1 | 5/2010 | Gant |
| 2010/0130582 A1 | 5/2010 | Gant et al. |
| 2010/0130615 A1 | 5/2010 | Gant |
| 2010/0136004 A1 | 6/2010 | Mei et al. |
| 2010/0143507 A1 | 6/2010 | Gant et al. |
| 2010/0159033 A1 | 6/2010 | Gant et al. |
| 2010/0159034 A1 | 6/2010 | Gant et al. |
| 2010/0166887 A1 | 7/2010 | Gant et al. |
| 2010/0166889 A1 | 7/2010 | Sanfilippo |
| 2010/0167988 A1 | 7/2010 | Gant et al. |
| 2010/0167989 A1 | 7/2010 | Gant |
| 2010/0179129 A1 | 7/2010 | Krishnan et al. |
| 2010/0190752 A1 | 7/2010 | Schiene et al. |
| 2010/0197610 A1 | 8/2010 | Lian et al. |
| 2010/0215739 A1 | 8/2010 | Najarian et al. |
| 2010/0215774 A1 | 8/2010 | Maibach |
| 2010/0216805 A1 | 8/2010 | Barlow et al. |
| 2010/0234331 A1 | 9/2010 | Xie et al. |
| 2010/0240601 A1 | 9/2010 | Piccariello et al. |
| 2010/0247625 A1 | 9/2010 | Geho et al. |
| 2010/0266711 A1 | 10/2010 | Gant et al. |
| 2010/0279991 A1 | 11/2010 | Liotta et al. |
| 2010/0285001 A1 | 11/2010 | Land et al. |
| 2010/0286275 A1 | 11/2010 | Zhang |
| 2010/0286762 A1 | 11/2010 | Gourdie et al. |
| 2010/0292217 A1 | 11/2010 | Belardinelli et al. |
| 2010/0310599 A1 | 12/2010 | Geho |
| 2010/0317572 A1 | 12/2010 | Mikkelsen et al. |
| 2010/0317633 A1 | 12/2010 | Xia et al. |
| 2010/0317730 A1 | 12/2010 | Shaya |
| 2010/0317731 A1 | 12/2010 | Shaya |
| 2010/0331762 A1 | 12/2010 | Wingeier et al. |
| 2011/0008468 A1 | 1/2011 | Haggarty et al. |
| 2011/0014296 A1 | 1/2011 | Chen et al. |
| 2011/0015663 A1 | 1/2011 | Aronne |
| 2011/0021564 A1 | 1/2011 | Sanfilippo |
| 2011/0053914 A1 | 3/2011 | Schiene et al. |
| 2011/0059170 A1 | 3/2011 | McKinney et al. |
| 2011/0065628 A1 | 3/2011 | Johnson et al. |
| 2011/0081426 A1 | 4/2011 | Rao et al. |
| 2011/0082407 A1 | 4/2011 | Aronne |
| 2011/0097326 A1 | 4/2011 | Luehrsen |
| 2011/0104315 A1 | 5/2011 | Sun et al. |
| 2011/0117070 A1 | 5/2011 | Aurora et al. |
| 2011/0117214 A1 | 5/2011 | Newbold et al. |
| 2011/0142914 A1 | 6/2011 | Persaud et al. |
| 2011/0178148 A1 | 7/2011 | Xia et al. |
| 2011/0195096 A1 | 8/2011 | Kindler et al. |
| 2011/0206780 A1 | 8/2011 | Gant et al. |
| 2011/0206782 A1 | 8/2011 | Zhang |
| 2011/0207661 A1 | 8/2011 | Chen et al. |
| 2011/0207718 A1 | 8/2011 | Bird |
| 2011/0212171 A1 | 9/2011 | Venkatesh et al. |
| 2011/0212944 A1 | 9/2011 | Liu et al. |
| 2011/0224196 A1 | 9/2011 | Wilson et al. |
| 2011/0230461 A1 | 9/2011 | Bhattacharya et al. |
| 2011/0236485 A1 | 9/2011 | Berner et al. |
| 2011/0244057 A1 | 10/2011 | Ehrenberg |
| 2011/0245208 A1 | 10/2011 | Diatchenko et al. |
| 2011/0245287 A1 | 10/2011 | Holaday et al. |
| 2011/0251248 A1 | 10/2011 | Lin et al. |
| 2011/0257260 A1 | 10/2011 | Rao et al. |
| 2011/0262535 A1 | 10/2011 | Najarian et al. |
| 2011/0281795 A1 | 11/2011 | Lin et al. |
| 2011/0287099 A1 | 11/2011 | Liang et al. |
| 2011/0287103 A1 * | 11/2011 | Liang et al. ............ 424/490 |
| 2011/0288079 A1 | 11/2011 | Kiel et al. |
| 2011/0294787 A1 | 12/2011 | Wenzel et al. |
| 2011/0301082 A1 | 12/2011 | Lin et al. |
| 2011/0306624 A1 | 12/2011 | Lin et al. |
| 2011/0312911 A1 | 12/2011 | Kats-Kagan et al. |
| 2011/0319388 A1 | 12/2011 | De Almeida et al. |
| 2012/0003312 A1 | 1/2012 | Nutalapati et al. |
| 2012/0020954 A1 | 1/2012 | Achiron et al. |
| 2012/0035105 A1 | 2/2012 | Geho et al. |
| 2012/0039881 A1 | 2/2012 | Mei et al. |
| 2012/0082659 A1 | 4/2012 | Land et al. |
| 2012/0109253 A1 | 5/2012 | Wingeier et al. |
| 2012/0114670 A1 | 5/2012 | Land et al. |
| 2012/0115849 A1 | 5/2012 | Demopulos et al. |
| 2012/0128683 A1 | 5/2012 | Shantha |
| 2012/0148689 A1 | 6/2012 | Maibach |
| 2012/0196881 A1 | 8/2012 | Najarian et al. |

FOREIGN PATENT DOCUMENTS

| | | |
|---|---|---|
| EP | 1 627 881 B1 | 10/2006 |
| EP | 1 731 524 A1 | 12/2006 |
| EP | 1 775 303 A1 | 4/2007 |
| EP | 1 977 736 A1 | 10/2008 |
| EP | 1 499 300 B1 | 3/2009 |
| WO | WO 98/00124 A1 | 1/1998 |
| WO | WO 98/00129 A2 | 1/1998 |
| WO | WO 98/15270 A1 | 4/1998 |
| WO | WO 99/44581 A2 | 9/1999 |
| WO | WO 00/01376 A2 | 1/2000 |
| WO | WO 00/23059 A2 | 4/2000 |
| WO | WO 00/32183 A1 | 6/2000 |
| WO | WO 00/42995 A2 | 7/2000 |
| WO | WO 00/44374 A1 | 8/2000 |
| WO | WO 00/61140 A1 | 10/2000 |

(56) References Cited

FOREIGN PATENT DOCUMENTS

| | | |
|---|---|---|
| WO | WO 00/06096 A2 | 11/2000 |
| WO | WO 00/66108 A2 | 11/2000 |
| WO | WO 01/27107 A2 | 4/2001 |
| WO | WO 01/89445 A1 | 11/2001 |
| WO | WO 01/96311 A2 | 12/2001 |
| WO | WO 01/96347 A1 | 12/2001 |
| WO | WO 02/00221 A1 | 1/2002 |
| WO | WO 02/053187 A2 | 7/2002 |
| WO | WO 02/078730 A2 | 10/2002 |
| WO | WO 02/083128 A1 | 10/2002 |
| WO | WO 02/087590 A1 | 11/2002 |
| WO | WO 02/096357 A2 | 12/2002 |
| WO | WO 02/098418 A1 | 12/2002 |
| WO | WO 03/020289 A1 | 3/2003 |
| WO | WO 03/020737 A1 | 3/2003 |
| WO | WO 03/026676 A1 | 4/2003 |
| WO | WO 03/037379 A1 | 5/2003 |
| WO | WO 03/039563 A1 | 5/2003 |
| WO | WO 03/041697 A1 | 5/2003 |
| WO | WO 03/070738 A2 | 8/2003 |
| WO | WO 03/072138 A1 | 9/2003 |
| WO | WO 03/0800072 A1 | 10/2003 |
| WO | WO 03/090723 A1 | 11/2003 |
| WO | WO 03/097038 A1 | 11/2003 |
| WO | WO 03/097046 A1 | 11/2003 |
| WO | WO 03/097656 A2 | 11/2003 |
| WO | WO 03/099273 A1 | 12/2003 |
| WO | WO 03/101380 A2 | 12/2003 |
| WO | WO 2004/002447 A2 | 1/2004 |
| WO | WO 2004/009015 A2 | 1/2004 |
| WO | WO 2004/009017 A2 | 1/2004 |
| WO | WO 2004/010970 A1 | 2/2004 |
| WO | WO 2004/026299 A1 | 4/2004 |
| WO | WO 2004/030637 A2 | 4/2004 |
| WO | WO 2004/054547 A1 | 7/2004 |
| WO | WO 2004/054965 A1 | 7/2004 |
| WO | WO 2004/058222 A1 | 7/2004 |
| WO | WO 2004/078161 A1 | 9/2004 |
| WO | WO 2004/078163 A2 | 9/2004 |
| WO | WO 2004/078769 A1 | 9/2004 |
| WO | WO 2004/089965 A2 | 10/2004 |
| WO | WO 2004/105682 A2 | 12/2004 |
| WO | WO 2004/110385 A2 | 12/2004 |
| WO | WO 2004/111015 A1 | 12/2004 |
| WO | WO 2005/000807 A2 | 1/2005 |
| WO | WO 2005/013894 A2 | 2/2005 |
| WO | WO 2005/016306 A2 | 2/2005 |
| WO | WO 2005/020957 A2 | 3/2005 |
| WO | WO 2005/020959 A2 | 3/2005 |
| WO | WO 2005/020961 A1 | 3/2005 |
| WO | WO 2005/030758 A1 | 4/2005 |
| WO | WO 2005/048979 A2 | 6/2005 |
| WO | WO 2005/048981 A1 | 6/2005 |
| WO | WO 2005/048990 A2 | 6/2005 |
| WO | WO 2005/049043 A1 | 6/2005 |
| WO | WO 2005/051358 A1 | 6/2005 |
| WO | WO 2005/051386 A1 | 6/2005 |
| WO | WO 2005/063248 A1 | 7/2005 |
| WO | WO 2005/063297 A2 | 7/2005 |
| WO | WO 2005/065648 A2 | 7/2005 |
| WO | WO 2005/070207 A1 | 8/2005 |
| WO | WO 2005/070461 A2 | 8/2005 |
| WO | WO 2005/072729 A1 | 8/2005 |
| WO | WO 2005/072732 A1 | 8/2005 |
| WO | WO 2005/073221 A1 | 8/2005 |
| WO | WO 2005/077925 A1 | 8/2005 |
| WO | WO 2005/079748 A2 | 9/2005 |
| WO | WO 2005/097125 A2 | 10/2005 |
| WO | WO 2005/099674 A1 | 10/2005 |
| WO | WO 2005/110405 A1 | 11/2005 |
| WO | WO 2005/113506 A1 | 12/2005 |
| WO | WO 2005/113519 A1 | 12/2005 |
| WO | WO 2006/007323 A2 | 1/2006 |
| WO | WO 2006/009403 A1 | 1/2006 |
| WO | WO 2006/014484 A2 | 2/2006 |
| WO | WO 2006/015930 A1 | 2/2006 |
| WO | WO 2006/017238 A1 | 2/2006 |
| WO | WO 2006/017341 A2 | 2/2006 |
| WO | WO 2006/017524 A2 | 2/2006 |
| WO | WO 2006/017537 A1 | 2/2006 |
| WO | WO 2006/019978 A2 | 2/2006 |
| WO | WO 2006/031491 A2 | 3/2006 |
| WO | WO 2006/031610 A2 | 3/2006 |
| WO | WO 2006/031676 A2 | 3/2006 |
| WO | WO 2006/044472 A1 | 4/2006 |
| WO | WO 2006/047204 A1 | 5/2006 |
| WO | WO 2006/047450 A2 | 5/2006 |
| WO | WO 2006/049933 A2 | 5/2006 |
| WO | WO 2006/067494 A1 | 6/2006 |
| WO | WO 2006/076632 A1 | 7/2006 |
| WO | WO 2006/076633 A1 | 7/2006 |
| WO | WO 2006/076796 A1 | 7/2006 |
| WO | WO 2006/082245 A1 | 8/2006 |
| WO | WO 2006/084176 A2 | 8/2006 |
| WO | WO 2006/088305 A1 | 8/2006 |
| WO | WO 2006/092691 A1 | 9/2006 |
| WO | WO 2006/097946 A1 | 9/2006 |
| WO | WO 2006/101950 A2 | 9/2006 |
| WO | WO 2006/102029 A2 | 9/2006 |
| WO | WO 2006/107903 A2 | 10/2006 |
| WO | WO 2006/113095 A2 | 10/2006 |
| WO | WO 2006/121363 A1 | 11/2006 |
| WO | WO 2006/127748 A1 | 11/2006 |
| WO | WO 2006/130522 A2 | 12/2006 |
| WO | WO 2007/002872 A2 | 1/2007 |
| WO | WO 2007/008551 A2 | 1/2007 |
| WO | WO 2007/008562 A2 | 1/2007 |
| WO | WO 2007/014929 A1 | 2/2007 |
| WO | WO 2007/016108 A1 | 2/2007 |
| WO | WO 2007/017764 A2 | 2/2007 |
| WO | WO 2007/022255 A2 | 2/2007 |
| WO | WO 2007/026224 A2 | 3/2007 |
| WO | WO 2007/032720 A1 | 3/2007 |
| WO | WO 2007/035425 A2 | 3/2007 |
| WO | WO 2007/038610 A2 | 4/2007 |
| WO | WO 2007/047351 A2 | 4/2007 |
| WO | WO 2007/048027 A2 | 4/2007 |
| WO | WO 2007/056366 A2 | 5/2007 |
| WO | WO 2007/056496 A1 | 5/2007 |
| WO | WO 2007/056497 A1 | 5/2007 |
| WO | WO 2007/063418 A2 | 6/2007 |
| WO | WO 2007/067341 A2 | 6/2007 |
| WO | WO 2007/075555 A2 | 7/2007 |
| WO | WO 2007/087154 A2 | 8/2007 |
| WO | WO 2007/087204 A2 | 8/2007 |
| WO | WO 2007/087448 A1 | 8/2007 |
| WO | WO 2007/089318 A2 | 8/2007 |
| WO | WO 2007/089557 A2 | 8/2007 |
| WO | WO 2007/089667 A1 | 8/2007 |
| WO | WO 2007/094825 A2 | 8/2007 |
| WO | WO 2007/099388 A1 | 9/2007 |
| WO | WO 2007/100902 A2 | 9/2007 |
| WO | WO 2007/100905 A2 | 9/2007 |
| WO | WO 2007/106862 A2 | 9/2007 |
| WO | WO 2007/108009 A1 | 9/2007 |
| WO | WO 2007/115997 A2 | 10/2007 |
| WO | WO 2007/117466 A2 | 10/2007 |
| WO | WO 2007/117549 A2 | 10/2007 |
| WO | WO 2007/119178 A2 | 10/2007 |
| WO | WO 2007/128349 A1 | 11/2007 |
| WO | WO 2007/130848 A2 | 11/2007 |
| WO | WO 2007/137164 A2 | 11/2007 |
| WO | WO 2007/137167 A2 | 11/2007 |
| WO | WO 2007/140191 A2 | 12/2007 |
| WO | WO 2007/143422 A2 | 12/2007 |
| WO | WO 2008/002816 A1 | 1/2008 |
| WO | WO 2008/002817 A1 | 1/2008 |
| WO | WO 2008/002818 A1 | 1/2008 |
| WO | WO 2008/002820 A2 | 1/2008 |
| WO | WO 2008/010231 A2 | 1/2008 |
| WO | WO 2008/027557 A2 | 3/2008 |
| WO | WO 2008/036798 A2 | 3/2008 |
| WO | WO 2008/061226 A2 | 5/2008 |
| WO | WO 2008/070670 A2 | 6/2008 |

(56) References Cited

FOREIGN PATENT DOCUMENTS

| | | |
|---|---|---|
| WO | WO 2008/061226 A3 | 7/2008 |
| WO | WO 2008/088820 A2 | 7/2008 |
| WO | WO 2008/089521 A1 | 7/2008 |
| WO | WO 2008/091692 A2 | 7/2008 |
| WO | WO 2008/091934 A2 | 7/2008 |
| WO | WO 2008/095086 A2 | 8/2008 |
| WO | WO 2008/095253 A1 | 8/2008 |
| WO | WO 2008/097976 A1 | 8/2008 |
| WO | WO 2008/098195 A2 | 8/2008 |
| WO | WO 2008/098195 A3 | 9/2008 |
| WO | WO 2008/106659 A2 | 9/2008 |
| WO | WO 2008/109343 A1 | 9/2008 |
| WO | WO 2008/115705 A2 | 9/2008 |
| WO | WO 2008/115797 A1 | 9/2008 |
| WO | WO 2008/106659 A3 | 10/2008 |
| WO | WO 2008/121882 A1 | 10/2008 |
| WO | WO 2008/122014 A1 | 10/2008 |
| WO | WO 2008/128126 A1 | 10/2008 |
| WO | WO 2008/128166 A1 | 10/2008 |
| WO | WO 2008/091692 A3 | 11/2008 |
| WO | WO 2008/095086 A3 | 11/2008 |
| WO | WO 2008/088820 A3 | 12/2008 |
| WO | WO 2008/148064 A1 | 12/2008 |
| WO | WO 2008/153632 A2 | 12/2008 |
| WO | WO 2008/156550 A2 | 12/2008 |
| WO | WO 2008/115705 A3 | 1/2009 |
| WO | WO 2008/128126 A8 | 1/2009 |
| WO | WO 2009/015236 A1 | 1/2009 |
| WO | WO 2009/018132 A2 | 2/2009 |
| WO | WO 2009/018326 A2 | 2/2009 |
| WO | WO 2009/021129 A1 | 2/2009 |
| WO | WO 2009/023292 A1 | 2/2009 |
| WO | WO 2009/023653 A2 | 2/2009 |
| WO | WO 2009/026241 A1 | 2/2009 |
| WO | WO 2009/018326 A3 | 3/2009 |
| WO | WO 2009/029308 A1 | 3/2009 |
| WO | WO 2009/035473 A2 | 3/2009 |
| WO | WO 2009/040818 A1 | 4/2009 |
| WO | WO 2009/042960 A1 | 4/2009 |
| WO | WO 2009/045443 A2 | 4/2009 |
| WO | WO 2009/054544 A1 | 4/2009 |
| WO | WO 2009/018132 A3 | 5/2009 |
| WO | WO 2009/018132 A9 | 6/2009 |
| WO | WO 2009/073843 A1 | 6/2009 |
| WO | WO 2008/153632 A3 | 7/2009 |
| WO | WO 2008/156550 A3 | 7/2009 |
| WO | WO 2009/080691 A2 | 7/2009 |
| WO | WO 2009/092049 A1 | 7/2009 |
| WO | WO 2009/080691 A3 | 8/2009 |
| WO | WO 2009/108837 A2 | 9/2009 |
| WO | WO 2009/126931 A2 | 10/2009 |
| WO | WO 2009/131692 A1 | 10/2009 |
| WO | WO 2009/132119 A2 | 10/2009 |
| WO | WO 2009/133128 A1 | 11/2009 |
| WO | WO 2009/133141 A2 | 11/2009 |
| WO | WO 2009/133142 A1 | 11/2009 |
| WO | WO 2008/091934 A3 | 12/2009 |
| WO | WO 2009/035473 A3 | 12/2009 |
| WO | WO 2009/045443 A3 | 12/2009 |
| WO | WO 2009/108837 A3 | 12/2009 |
| WO | WO 2009/133141 A3 | 12/2009 |
| WO | WO 2009/152189 A1 | 12/2009 |
| WO | WO 2009/152190 A1 | 12/2009 |
| WO | WO 2010/002869 A1 | 1/2010 |
| WO | WO 2010/005507 A1 | 1/2010 |
| WO | WO 2010/009335 A1 | 1/2010 |
| WO | WO 2009/132119 A3 | 2/2010 |
| WO | WO 2010/013240 A1 | 2/2010 |
| WO | WO 2010/015029 A1 | 2/2010 |
| WO | WO 2010/015567 A2 | 2/2010 |
| WO | WO 2009/126931 A3 | 3/2010 |
| WO | WO 2010/025931 A2 | 3/2010 |
| WO | WO 2010/030722 A1 | 3/2010 |
| WO | WO 2010/036977 A2 | 4/2010 |
| WO | WO 2010/044736 A1 | 4/2010 |
| WO | WO 2010/045416 A2 | 4/2010 |
| WO | WO 2010/048358 A2 | 4/2010 |
| WO | WO 2009/040818 A9 | 5/2010 |
| WO | WO 2010/057104 A2 | 5/2010 |
| WO | WO 2010/059639 A2 | 5/2010 |
| WO | WO 2010/060037 A2 | 5/2010 |
| WO | WO 2010/060041 A2 | 5/2010 |
| WO | WO 2010/060070 A2 | 5/2010 |
| WO | WO 2010/071750 A1 | 6/2010 |
| WO | WO 2010/075086 A2 | 7/2010 |
| WO | WO 2010/080976 A1 | 7/2010 |
| WO | WO 2010/088061 A1 | 8/2010 |
| WO | WO 2010/093535 A1 | 8/2010 |
| WO | WO 2010/098888 A1 | 9/2010 |
| WO | WO 2010/098948 A1 | 9/2010 |
| WO | WO 2010/098994 A1 | 9/2010 |
| WO | WO 2010/099217 A1 | 9/2010 |
| WO | WO 2010/113096 A1 | 10/2010 |
| WO | WO 2010/118291 A2 | 10/2010 |
| WO | WO 2010/132696 A1 | 11/2010 |
| WO | WO 2010/147830 A2 | 12/2010 |
| WO | WO 2011/008298 A2 | 1/2011 |
| WO | WO 2011/009115 A2 | 1/2011 |
| WO | WO 2011/011420 A2 | 1/2011 |
| WO | WO 2011/023392 A1 | 3/2011 |
| WO | WO 2011/038210 A2 | 3/2011 |
| WO | WO 2011/041632 A2 | 4/2011 |
| WO | WO 2011/047383 A1 | 4/2011 |
| WO | WO 2011/050008 A2 | 4/2011 |
| WO | WO 2011/054759 A1 | 5/2011 |
| WO | WO 2011/060363 A2 | 5/2011 |
| WO | WO 2011/075688 A1 | 6/2011 |
| WO | WO 2011/085181 A1 | 7/2011 |
| WO | WO 2011/085256 A2 | 7/2011 |
| WO | WO 2011/107749 A2 | 9/2011 |
| WO | WO 2011/107750 A2 | 9/2011 |
| WO | WO 2011/107755 A2 | 9/2011 |
| WO | WO 2011/107855 A2 | 9/2011 |
| WO | WO 2011/114271 A1 | 9/2011 |
| WO | WO 2011/119953 A1 | 9/2011 |
| WO | WO 2011/120044 A1 | 9/2011 |
| WO | WO 2011/123610 A2 | 10/2011 |
| WO | WO 2011/126910 A2 | 10/2011 |
| WO | WO 2011/138421 A1 | 11/2011 |
| WO | WO 2011/143721 A1 | 11/2011 |
| WO | WO 2011/149757 A1 | 12/2011 |
| WO | WO 2011/163612 A1 | 12/2011 |
| WO | WO 2011/163619 A1 | 12/2011 |
| WO | WO 2012/022730 A1 | 2/2012 |
| WO | WO 2012/033874 A1 | 3/2012 |
| WO | WO 2012/056372 A1 | 5/2012 |
| WO | WO 2012/064667 A2 | 5/2012 |
| WO | WO 2012/074561 A2 | 6/2012 |
| WO | WO 2012/098245 A1 | 7/2012 |
| WO | WO 2012/100248 A1 | 7/2012 |
| WO | WO 2012/100347 A1 | 8/2012 |
| WO | WO 2012/103520 A1 | 8/2012 |

OTHER PUBLICATIONS

Cramer et al., "The relationship between poor medication compliance and seizures," 2002 *Epilepsy Behav.* 3:38-42.

Cydex website. Available online [retrieved on Apr. 21, 2008]. Retrieved from the Internet: <http://www.cydexinc.com/captisol.asp>; 1 page.

Dib, "Focus on topiramate in neuropathic pain" *Current Medical Research and Opinion*, Dec. 1, 2004, 20 (12) p. 1857-61.

Doose et al., "Single-dose pharmacokinetics and effect of food on the bioavailability of topiramate, a novel antiepileptic drug," 1996 *J Clin Pharmacol.* 36:884-91.

Food and Drug Administration, "Guidance for Industry. Extended Release Oral Dosage Forms: Development, Evaluation, and Application of In Vitro/In Vivo Correlations," U.S. Department of Health and Human Services, Center for Drug Evaluation and Research (CDER). Sep. 1997.

Food and Drug Administration, "Guidance for industry: Food-effect bioavailability and fed bioequivalence studies," Dec. 2002.

Food and Drug Administration, "Guidance for industry: Bioavailability and bioequivalence studies for orally administered drug products—general considerations," Mar. 2003.

(56) References Cited

OTHER PUBLICATIONS

Garnett, "Clinical pharmacology of topiramate: a review," 2000 *Epilepsia* 41(Supp 1):S61-5.

Halvorsen et al., "Pharmacokinetic Equivalence between Immediate-Release Topiramate and USL255, A Novel Extended-Release Formulation of Topiramate," poster presented at the *64th Annual Meeting of the American Epilepsy Society*; San Antonio, Texas: Dec. 3-7, 2010.

Halvorsen et al., "Extended-Release Topiramate (USL255) Exhibits Linear Dose-Proportional Pharmacokinetic Characteristics," poster presented at the *65th Annual Meeting of the American Epilepsy Society*; Baltimore, MD: Dec. 2-6, 2011.

Halvorsen et al., "Establishing Maximum Tolerated Dose and Dose-Proportionality in Extended-Release Topiramate (USL255)," poster presented at the *66th Annual Meeting of the American Epilepsy Society*; San Diego, CA: Nov. 30-Dec. 4, 2012.

Halvorsen et al., "Extended-Release Topiramate (USL255) Exhibits Linear Dose-Proportional Pharmacokinetic Characteristics," Conference Abstract No. P06.128. *62nd Annual Meeting of the American Academy of Neurology (AAN)*; New Orleans, LA: Apr. 22-27, 2012. Published online: *Neurology* 2012;78(suppl 1): P06.128. [retrieved on May 6, 2013]. Retrieved from the Internet: <http://www.neurology.org/cgi/content/meeting_abstract/78/1_MeetingAbstracts/P06.128>; 2 pages.

Hirst et al., "Gastrointestinal performance of the Microtrol extended release drug delivery technology," *Proceed. Int'l Symp. Control. Rel. Bioact. Mater.*, 26 (Revised Jul. 1999) Controlled Release Society, Inc.

"Johnson & Johnson to Acquire TransForm Pharmaceuticals" Press Release dated Mar. 9, 2005. Available on the J&J website [retrieved on Apr. 22, 2008]. Retrieved from the Internet: <http://www.investor.jnj.com/releasedetail.cfm?ReleaseID=157580&textOnly=false>; 2 pages.

Lambrecht et al., "Development and Optimization of Extended-Release Formulations of Topiramate," poster presented at the *64th Annual Meeting of the American Epilepsy Society*; San Antonio, Texas: Dec. 3-7, 2010.

Lambrecht et al., "Development and optimization of extended-release formulations of topiramate," Abstract No. 1.116 presented at the *63rd Annual Meeting of the American Academy of Neurology (AAN)*; Honolulu, HI: Apr. 9-16, 2011.

Lambrecht et al., "Pharmacokinetic Equivalence between Immediate-Release and Extended-Release Topiramate," Poster Abstract No. M710 presented at the *136th Annual Meeting of the American Neurological Association* Sep. 25-27, 2011: San Diego, CA. Published in Oct. 2011 *Ann Neurol.* 70 (Suppl. 15):S93-S102.

Lambrecht et al., "Steady-State Pharmacokinetics of USL255, an Extended-Release Formulation of Topiramate," poster presented at the *65th Annual Meeting of the American Epilepsy Society*; Baltimore, MD: Dec. 2-6, 2011.

Lambrecht et al., "Comparative pharmacokinetic analysis of USL255, a new once-daily extended-release formulation of topiramate," 2011 *Epilepsia* 52(10):1877-1883. Available online on Jul. 19, 2011.

Nahata et al., "Topiramate stability in two oral suspensions stored in plastic prescription bottles at two temperatures" *46th American Society of Health-System Pharmacists (ASHP) Midyear Clinical Meeting*, Dec. 4-8, 2001: New Orleans, LA. v36, p. P-77R.

Rosenstock et al., "A randomized, double-blind, placebo-controlled, multicenter study to assess the efficacy and safety of topiramate controlled release in the treatment of obese type 2 diabetic patients" *Diabetes Care*, Jun. 2007, 30 (6) p. 148-146.

Shank et al., "Plasma and whole blood pharmacokinetics of topiramate: the role of carbonic anhydrase," Feb. 2005 *Epilepsy Res.* 63(2-3):103-112.

Smith et al., "Confidence interval criteria for assessment of dose proportionality," Oct. 2000 *Pharm Res.* 17(10):1278-1283.

Styslo-Zalasik et al., "Determination of topiramate and its degradation product in liquid oral solutions by high performance liquid chromatography with a chemiluminescent nitrogen detector," *J. Pharm. Biomed. Anal.*, 2005, 37(3):529-34.

Syed et al., "Extended-release lamotrigine in the treatment of patients with epilepsy," 2010 *Expert Opin Pharmacother*. 11:1579-85.

Todd et al., "The Effect of Food on the Bioavailablity of USL255 A Novel Extended-Release Formulation of Topiramate," poster presented at the *64th Annual Meeting of the American Epilepsy Society*; San Antonio, Texas: Dec. 3-7, 2010.

Tonstad et al., "Efficacy and safety of topiramate in the treatment of obese subjects with essential hypertension," Jul. 15, 2005 *American Journal of Cardiology* 96(2):243-51.

Topamax [Prescribing Information]. Titusville, NJ: Janssen Pharmaceuticals, revised 2012. 46 pages.

Treiman, "Management of refractory complex partial seizures: current state of the art," May 25, 2010 *Neuropsychiatr Dis Treat*. 6:297-308.

World Health Organization. Epilepsy Fact Sheet; last updated Oct. 2012. http://www.who.int/mediacentre/factsheets/fs999/en/index.html. Accessed May 6, 2013.

Yin et al., "Optimizing first-time-in-human trial design for studying dose proportionality," 2001 *Drug Information Journal.* 35:1065-1078.

Nahata et al., "Topiramate stability in two oral suspensions stored in plastic prescription bottles at two temperatures" Poster abstract No. P-77R; presented as the *46th American Society of Health-System Pharmacists (ASHP) Midyear Clinical Meeting*, Dec. 4-8, 2001; New Orleans, LA. v36.

\* cited by examiner

EXTENDED-RELEASE TOPIRAMATE CAPSULES

CONTINUING APPLICATION DATA

This application claims the benefit of U.S. Provisional Application Ser. No. 61/779,576, filed Mar. 13, 2013, and also claims the benefit of U.S. Provisional Application Ser. No. 61/788,880, filed Mar. 15, 2013, each of which is incorporated by reference herein.

BACKGROUND

The pharmaceutical industry employs a variety of dosage formulations for orally administering medicinal agents to patients. Typical formulations for oral administration include liquid solutions, emulsions, or suspensions, as well as solid forms such as capsules or tablets (as used herein, the term "tablet" means any shaped and compressed solid dosage form, including caplets).

Efficacy of a drug product often depends on patient compliance with a dosing schedule. Therefore, one per day, extended-release, dosages have better efficacy over the long term than multidose regimens.

SUMMARY

The present disclosure provides solid dosage formulations of topiramate[2,3:4,5-bis-O-(1-methylethylidene)-β-D-fructopyranose sulfamate], particularly capsules, containers including such capsules, and methods of dosing.

In one embodiment, the present disclosure provides an extended-release formulation that is dosed once-per-day, in the form of a capsule.

In one embodiment, the present disclosure provides an extended-release topiramate capsule that includes a capsule shell and a single population of coated particles contained within the capsule shell, wherein each coated particle includes a core and a coating thereon. In certain embodiments, the particles, whether coated or uncoated, are spherical.

Each particle core includes a homogeneous mixture including topiramate throughout the core. In certain embodiments, each particle core also includes a filler and/or a binder (preferably, both a filler and a binder) in the homogeneous mixture.

The coating includes a release controlling agent. In certain embodiments, the coating also includes a pore former and/or a plasticizer.

In one embodiment, an extended-release topiramate capsule is provided that includes: a capsule shell containing a single population of coated particles; wherein each coated particle includes a core and a coating thereon; wherein each particle core includes a homogeneous mixture throughout its core, the mixture including: 40 wt-% to 50 wt-% of topiramate, based on the total weight of an uncoated particle core; 45 wt-% to 55 wt-% of one or more filler(s), based on the total weight of an uncoated particle core; and 3 wt-% to 7 wt-% of one or more binder(s), based on the total weight of an uncoated particle core; wherein the coating includes: 55 wt-% to 65 wt-% of one or more release control agent(s), based on the total weight of the coating; 20 wt-% to 25 wt-% of one or more pore former(s), based on the total weight of the coating; and 10 wt-% to 20 wt-% of one or more plasticizer(s), based on the total weight of the coating; wherein the particles are coated in an amount sufficient to provide a (coating) weight gain of 8% to 14%.

As used herein, the terms "topiramate active agent" and "active agent of topiramate" and "topiramate" are synonymous and are used interchangeably throughout the specification to refer to the compound 2,3:4,5-bis-O-(1-methylethylidene)-β-D-fructopyranose sulfamate. Included within these terms are also pharmaceutically acceptable salts thereof as well as polymorphs, solvates, hydrates, dehydrates, co-crystals, anhydrous, and amorphous forms thereof.

The term "extended-release" means release of an active agent over a period of time, which is much longer than the release from an immediate release formulation, which usually releases more than 80% of the active agent in 60 minutes or less.

The term "therapeutically effective amount" as used herein means that amount of active compound that elicits the biological or medicinal response in a tissue, system, animal or human that is being sought by a researcher, veterinarian, medical doctor or other clinician, which includes alleviation and/or prevention of the symptoms of the condition being treated.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a particle core that comprises "a" binder can be interpreted to mean that the particle core includes "one or more" binders. Similarly, a coating comprising "a" pore former can be interpreted to mean that the composition includes "one or more" pore formers.

As used herein, the term "or" is generally employed in its usual sense including "and/or" unless the content clearly dictates otherwise.

The term "and/or" means one or all of the listed elements or a combination of any two or more of the listed elements (e.g., preventing and/or treating an affliction means preventing, treating, or both preventing and treating an affliction).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present disclosure provides solid dosage formulations of topiramate [2,3:4,5-bis-O-(1-methylethylidene)-β-D-fructopyranose sulfamate]. Such solid dosage formulations are extended-release once-per-day dosage capsules (i.e., designed for administration once per day).

In one embodiment, the present disclosure provides an extended-release topiramate capsule that includes a capsule shell and a single population of coated particles contained within the capsule shell. In this context, "a single population" means that all the particles in one capsule are the same (within reasonable manufacturing variability) with respect to composition. In this context, "same" means the particles in one capsule are made in a single batch process or in multiple batches using identical processes.

The use of a single population of particles in any one capsule provides significant advantages from a manufacturing (e.g., quality and cost) perspective. For example, different populations of particles (e.g., beads), having different compositions, do not need to be manufactured for one product.

Furthermore, in certain embodiments, the capsules of the present disclosure do not include an immediate release component in any significant amount. Typically, capsules of the present invention are free of an immediate-release component.

Each coated particle includes a core and a coating thereon. In certain embodiments, the particles, whether coated or uncoated, are spherical, as defined in greater detail below.

Each particle core includes a homogeneous mixture including topiramate throughout the core. In certain embodiments, each particle core also includes a filler and/or a binder (preferably, both a filler and a binder) in the homogeneous mixture.

The coating on each core includes a release controlling agent. In certain embodiments, the coating also includes a pore former and/or a plasticizer.

In one embodiment, the present disclosure provides a solid dosage formulation that includes a capsule including core particles with a coating thereon. The core particles include the active agent. The core particles can also include a filler and/or a binder (preferably, both a filler and a binder). The coating includes a release-controlling agent. The coating can also include a pore former and/or a plasticizer.

In certain embodiments, the particles, whether coated or uncoated, are spherical. In this context, the term "spherical" refers to particles that are generally rounded by visual inspection. They may or may not be perfectly spherical. A representative population of spherical particles (i.e., beads) typically has an average sphericity of at least 0.7. In certain embodiments, the average sphericity of a representative population of particles is at least 0.75, and in certain embodiments at least 0.8. A preferred sphericity is 0.8. Sphericity can be determined by use of a digital microscope and a two-dimensional image analysis software (e.g., such as that by Soft Imaging System GmbH, version 5.0 Build 1054).

In certain embodiments, the particle size (which is typically the diameter of a spherical particle) of the coated particles is at least 500 μm (microns). In certain embodiments, the particle size of the coated particles is up to 1300 μm. In certain embodiments, the majority of the particles in a capsule are typically in a range of 700 μm to 1000 μm.

The rate of particle dissolution is typically dependent on the coating weight, which can be adjusted during manufacture. In certain embodiments, the particles are coated in an amount sufficient to provide a weight gain of at least 2%, or at least 4%, or at least 6%, or at least 8%, or at least 9%, or at least 10%. In certain embodiments, the particles are coated in an amount sufficient to provide a weight gain of up to 30%, or up to 25%, or up to 20%, or up to 15%, or up to 12%. Preferably, the particles are coated in an amount sufficient to provide a weight gain of 10% to 12%. In certain embodiments, the particles are coated in an amount sufficient to provide a weight gain of 8% to 14%.

In this context, "weight gain" is defined as the theoretical weight gain of a population of particles as a result of coating, assuming 100% coating efficiency. Thus, "weight gain" refers to coating weight gain. As an example, 100 grams of uncoated particles (e.g., beads) coated to a theoretical weight gain of 8% means that an amount of coating solution having 8 grams (g) of non-volatile components, e.g., release controlling agent, pore former, and plasticizer, was applied to the uncoated beads in a coating step, but there may be some losses in the manufacturing process.

Suitable active agents within the particle core include topiramate (2,3:4,5-bis-O-(1-methylethylidene)-β-D-fructopyranose sulfamate). "Topiramate" refers to 2,3:4,5-bis-O-(1-methylethylidene)-β-D-fructopyranose sulfamate as well as pharmaceutically acceptable salts of topiramate, including without limitation, topiramate sodium, topiramate lithium, topiramate potassium, as well as polymorphs, solvates, hydrates, dehydrates, co-crystals, anhydrous, and amorphous forms thereof. Topiramate can be purchased from commercial sources. It is presently available for marketing as an immediate-release tablet product (as TOPAMAX) for certain seizure indications and migraine prophylaxis.

An amount of topiramate active agent is included within a capsule in an amount sufficient to deliver the desired dose. Alternatively stated, a therapeutically effective amount of topiramate is included within a capsule. A capsule can include a topiramate active agent in an amount of at least 10 weight percent (wt-% or % w/w), or at least 25 wt-%, or at least 35 wt-%, or at least 40 wt-%, or at least 44 wt-%, based on the total weight of an uncoated particle core. A capsule can include a topiramate active agent in an amount of up to 80 wt-%, or up to 50 wt-%, or up to 46 wt-%, based on the total weight of an uncoated particle core. In certain embodiments, the particle cores of the capsules of the present disclosure include 40 wt-% to 50 wt-% topiramate active agent, based on the total weight of an uncoated particle core. In certain embodiments, the particle cores of the capsules of the present disclosure include 44 wt-% to 46 wt-% topiramate active agent, based on the total weight of an uncoated particle core.

The active agent can be homogeneously mixed within a particle core that includes one or more fillers and/or binders.

One or more stabilizers can also be included in the particle core. Inclusion of a stabilizer may help maintain the potency of topiramate over time.

Herein, for any component specified, if there are multiple grades (e.g., molecular weights) of such component, recitation of the component implies any or all of such variations.

Suitable fillers for use in the particle cores include, but are not limited to, microcrystalline cellulose, dibasic calcium phosphate, lactose, tribasic calcium phosphate, mannitol, other suitable carbohydrates (e.g., other sugars or starches). Combinations of fillers can be used if desired. Preferably, microcrystalline cellulose is used as a filler (such as that available from JRS Pharma under the trade designation EMCOCEL 90M).

One or more fillers can be used in an amount of at least 10 wt-%, or at least 25 wt-%, or at least 45 wt-%, or at least 48 wt-%, based on the total weight of the uncoated particle core. One or more fillers can be used in an amount of up to 85 wt-%, or up to 75 wt-%, or up to 55 wt-%, or up to 52 wt-%, based on the total weight of the uncoated particle core. In certain embodiments, the particle cores of the capsules of the present disclosure include 45 wt-% to 55 wt-% filler(s), based on the total weight of an uncoated particle core. In certain embodiments, the particle cores of the capsules of the present disclosure include 48 wt-% to 52 wt-% filler(s), based on the total weight of an uncoated particle core.

Suitable binders for use in the particle core include, but are not limited to, hydroxypropyl methylcellulose (i.e., hypromellose or "HPMC"), methylcellulose, carboxymethylcellulose, sodium carboxymethylcellulose, hydroxypropyl cellulose, hydroxyethylcellulose, polyvinyl pyrrolidine (i.e., povidone), starch (e.g., pregelatinized starch), and natural gum (e.g., acacia gum, sodium alginate, guar gum, xanthan gum). Combinations of binders can be used if desired. Preferably, hydroxypropyl methylcellulose (hypromellose 2910) is used as a binder (such as that available from The Dow Chemical Company under the trade designation METHOCEL E5 Premium).

One or more binders can be used in an amount of at least 1 wt-%, or at least 2 wt-%, or at least 3 wt-%, or at least 4 wt-%, based on the total weight of the uncoated particle core. One or more binders can be used in an amount of up to 10 wt-%, or up to 9 wt-%, or up to 8 wt-%, or up to 7 wt-%, or up to 6 wt-%, based on the total weight of the uncoated particle core. In certain embodiments, the particle cores of the capsules of the present disclosure include 3 wt-% to 7 wt-% binder(s), based on the total weight of an uncoated particle core. In certain embodiments, the particle cores of the capsules of the present disclosure include 4 wt-% to 6 wt-% binder(s), based on the total weight of an uncoated particle core.

Particles described herein can further include a stabilizer, preferably in the core. Suitable stabilizers for use in the particle core include, but are not limited to, calcium hydroxide, calcium carbonate, sodium bicarbonate, magnesium carbonate, and other alkali or alkaline earth metal hydroxides and carbonates. Combinations of stabilizers can be used if desired. Preferably, calcium carbonate is used as a stabilizer.

One or more stabilizers can be used in an amount of at least 1 wt-%, or at least 2 wt-%, based on the total weight of the particle core. One or more stabilizers can be used in an amount of up to 10 wt-%, or up to 5 wt-%, based on the total weight of the particle core. In certain embodiments, the particle cores of the capsules of the present disclosure include 2 wt-% to 10 wt-% stabilizer(s), based on the total weight of an uncoated particle core.

Suitable release controlling agents for use in the coating on the particle core include, but are not limited to, ethylcellulose, polyvinyl acetate, polyacrylate and polymethacrylate (e.g., Ammonio Methacrylate Copolymer, Type A and Type B; Ethyl Acrylate and Methyl Methacrylate Copolymer), and copolymers thereof. Combinations of release controlling agents can be used if desired. Preferably, ethylcellulose (such as that available from The Dow Chemical Company under the trade designation ETHOCEL Standard 10 Premium) is used as a release controlling agent.

One or more release controlling agents can be used in an amount of at least 45 wt-%, or at least 50 wt-%, or at least 55 wt-%, or at least 60 wt-%, based on the total weight of the coating. One or more release controlling agents can be used in an amount of up to 80 wt-%, or up to 70 wt-%, or up to 65 wt-%, or up to 62 wt-%, based on the total weight of the coating. In certain embodiments, the particle coatings include 55 wt-% to 65 wt-% release control agent(s), based on the total weight of the coating. In certain embodiments, the particle coatings include 60 wt-% to 62 wt-% release control agent(s), based on the total weight of the coating.

Herein, "based on the total weight of the coating" means the total weight of the non-volatile components of the coating (e.g., release controlling agent, pore former, and plasticizer).

Pore formers that are suitable for use in the coating formulation include, but are not limited to, hypromellose, hydroxypropyl cellulose, methylcellulose, hydroxyethylcellulose, carboxymethylcellulose, sodium carboxymethylcellulose, polyethylene glycol, guar gum, xanthan gum, sodium alginate, povidone (i.e., polyvinylpyrrolidone), crospovidone, sodium starch glycolate, croscarmellose sodium, starch (e.g., pregelatinized starch), carbohydrates (e.g., mannitol, glucose, sucrose, fructose, mannose, galactose, sorbitol, and dextran), sodium chloride, potassium chloride, and calcium chloride. Preferred pore formers for use in the coating on the particle core include, but are not limited to, hydroxypropyl methylcellulose ("HPMC" such as hypromellose 2910 USP available under the trade name METHOCEL E5 Premium, METHOCEL E15 Premium), carboxymethylcellulose, methylcellulose, croscarmellose sodium, povidone, sodium starch glycolate, starch (e.g., pregelatinized starch), alginic acid, guar gum, and polyethylene glycol. Combinations of pore formers can be used if desired. Preferably, hydroxypropyl methylcellulose (hypromellose 2910) is used as a pore former (such as that available from The Dow Chemical Company under the trade designation METHOCEL E5 Premium).

One or more pore formers can be used in an amount of at least 5 wt-%, or at least 10 wt-%, or at least 15 wt-%, or at least 20 wt-%, or at least 22 wt-%, based on the total weight of the coating. One or more pore formers can be used in an amount of up to 30 wt-%, or up to 26 wt-%, or up to 25 wt-%, or up to 24 wt-%, based on the total weight of the coating. In certain embodiments, the particle coatings include 20 wt-% to 25 wt-% pore former(s), based on the total weight of the coating. In certain embodiments, the particle coatings include 22 wt-% to 24 wt-% pore former(s), based on the total weight of the coating.

Suitable plasticizers for use in the coating on the particle core include, but are not limited to, diethyl phthalate, triethyl citrate, dibutyl sebacate, polyethylene glycol, triacetin, tributyl citrate, glycerol, and propylene glycol. Combinations of plasticizers can be used if desired. Preferably, diethyl phthalate is used as a plasticizer.

One or more plasticizers can be used in an amount of at least 5 wt-%, or at least 10 wt-%, or at least 15 wt-%, based on the total weight of the coating. One or more plasticizers can be used in an amount of up to 30 wt-%, or up to 20 wt-%, or up to 18 wt-%, based on the total weight of the coating. In certain embodiments, the particle coatings include 10 wt-% to 20 wt-% plasticizer(s), based on the total weight of the coating. In certain embodiments, the particle coatings include 15 wt-% to 18 wt-% plasticizer(s), based on the total weight of the coating.

The coating solution typically includes the "solids" or non-volatile components (e.g., ethylcellulose, hypromellose 2910 and diethyl phthalate) along with solvents, such as a mixture of alcohol and water, such that the concentration of the non-volatile components in the coating solution is 5 wt-% to 10 wt-%. In an exemplary solution, the solvents are dehydrated alcohol and purified water in a weight ratio of 3.7:1.

Particles can be coated with a coating composition as described herein using conventional techniques known to one of skill in the art. Briefly, such coating techniques include bottom-spray fluid-bed coating (e.g., Würster), top-spray fluid-bed coating, and tangential-spray fluid-bed coating. Typically, such methods result in a coating that is substantially uniform on each individual particle.

An amount of coated particles sufficient to deliver the desired dose may be encapsulated into a capsule of any desirable size, for example, a size 000, 00, 0el, 0, 1, 2, 3, 4, or 5.

Components of a suitable capsule shell include, but are not limited to, hydroxypropyl methylcellulose and gelatin. Preferably, a capsule shell is a hydroxypropyl methylcellulose (HPMC) shell (e.g., at least 90 wt-% HPMC, based on the weight of the shell). Typically, commercially available HPMC capsules include small amounts of water, colorants (e.g., $TiO_2$ and iron oxides), and optionally gelling agents and gelling promoters. They have relatively low moisture content, making them suitable for moisture-sensitive materials. Such capsules resist breakage even at low moisture levels. HPMC capsules typically exhibit low solubility in ethanol, particularly in acidic media such as found in the stomach. Encapsulation of the particles of the present disclosure in such an HPMC capsule shell preferably reduces dose dumping (and immediate release) of topiramate from the coated particles (see "Alcohol Dose Dumping" experiment in the Examples Section).

The chemical stability of capsules of the present disclosure typically depends on humidity and/or water activity. Thus, it can be desirable to reduce exposure to excessive moisture during storage. This can be done, for example, by storing the capsules of the present disclosure in a container, particularly a sealed container that includes a desiccant. If a desiccant is used, the ratio of weight of desiccant to weight of filled capsules can be at least 0.01, or at least 0.1, or at least 0.25, and can be up to 0.9.

Suitable containers include, for example, high density polyethylene (HDPE). Such containers can be bottles with screw caps, or the like. Preferably, such bottles are sealed, particularly induction sealed, in addition to a boundary layer provided by the screw cap.

Suitable desiccants include, for example, silica gel, bentonite clay, and molecular sieve. Combinations of desiccants can be used if desired.

Capsules of the present disclosure are preferably chemically stable. That is, capsules of the present disclosure retain a potency of at least 90% after a given time period of storage in a sealed container at 25° C. and 60% relative humidity (RH). They also demonstrate little or no decomposition after a given time period such that no more than 2000 parts per million (ppm) each of sulfate or sulfamate decomposition products are produced (see Examples Section). In this context, the given time period is preferably at least 12 months (typically, without any packaging), or at least 24 months (potentially, without any packaging, although packaging, e.g., sealed container and desiccant as described herein would be preferred to achieve chemical stability for this length of time), or at least 36 months (typically, with packaging, e.g., sealed container and desiccant as described herein).

The present disclosure also provides methods of dosing a subject in need thereof. Such dosing could be for the treatment of convulsions (e.g., convulsions associated with epilepsy). Such dosing could be for prophylactic treatment, for example, of a migraine. Such dosing methods include administering a topiramate capsule. In certain embodiments, once-per-day dosing of the capsule of the present disclosure occurs in the morning. In certain embodiments, once-per-day dosing of the capsule of the present disclosure occurs in the evening.

In certain embodiments, the extended-release topiramate capsules of the present disclosure, when dosed to a healthy human subject once daily (e.g., in the morning or evening), achieves at steady-state, an $AUC_{0-24h}$, $C_{max}$, and $C_{min}$ in the subject's plasma that are within the 80% to 125% bioequivalence criteria compared to immediate-release topiramate dosed twice per day (where the once-daily dose contains 2× the topiramate active agent as the individual immediate-release doses).

In this context, two treatments are bioequivalent at steady state (i.e., they are not different from one another) if the 90% confidence interval (CI) of the least squares geometric mean of one formulation-to-another formulation (e.g., capsules of the present disclosure to once-daily dose topiramate) ratio for each pharmacokinetic (PK) parameter (e.g., $AUC_{0-24h}$, $C_{max}$, and $C_{min}$) is completely contained within the 80-125% interval.

In certain embodiments, the extended-release topiramate capsules of the present disclosure, when dosed to a healthy human subject once daily in the morning, achieves at steady-state, a reduction of fluctuation index of at least 15% compared to immediate-release topiramate dosed twice per day. In certain embodiments, the reduction of fluctuation index is at least 20% compared to immediate-release topiramate dosed twice per day. In certain embodiments, the reduction of fluctuation index is at least 25% compared to immediate-release topiramate dosed twice per day.

In certain embodiments, the extended-release topiramate capsules of the present disclosure, when dosed to a healthy human subject once daily in the morning, achieves at steady-state, a $C_{min}$ in the subject's plasma that is higher than the $C_{min}$ compared to immediate-release topiramate dosed twice per day.

In certain embodiments, the extended-release topiramate capsules of the present disclosure, when given as a single-dose to a healthy human subject, achieves an $AUC_{0-inf}$ of 170 to 210 h·μg/mL within a 95% confidence interval, and a $C_{max}$ of 2 to 4 μg/mL within a 95% confidence interval.

Capsules of the present disclosure demonstrate a reduced level of side effects compared to other topiramate products. For example, in certain embodiments, the extended-release topiramate capsules of the present disclosure, when dosed once daily to a population of human patients suffering from epilepsy, achieves a reduction in incidence of at least one side effect compared to immediate-release topiramate dosed at the same total daily dose divided twice per day. This comparison is based on the extended-release topiramate capsules of the present disclosure compared to placebo, and the immediate-release topiramate (TOPAMAX) compared to placebo. The term "incidence" refers to the percentage of patients who experience a new side effect during the study. The at least one side effect includes somnolence, dizziness, ataxia, disturbance in attention, memory impairment, cognitive disorder, and psychomotor slowing.

LIST OF EXEMPLARY EMBODIMENTS

1. An extended-release topiramate capsule comprising:
    a capsule shell comprising (or consisting essentially of, or consisting of) a single population of coated particles;
        wherein each coated particle comprises a core and a coating thereon;
        wherein each particle core comprises a homogeneous mixture comprising topiramate throughout its core; and
        wherein the coating comprises one or more release controlling agent(s).
2. The capsule of embodiment 1 wherein:
    each particle core comprises a homogeneous mixture comprising:
        topiramate;
        one or more filler(s); and
        one or more binder(s); and
    the coating comprises:
        one or more release controlling agent(s);
        one or more pore former(s); and
        one or more plasticizer(s).
3. An extended-release topiramate capsule comprising (or consisting essentially of, or consisting of):
    a capsule shell comprising (or consisting essentially of, or consisting of) a single population of coated particles;
        wherein each coated particle comprises (or consists essentially of, or consists of) a core and a coating thereon;
        wherein each particle core comprises (or consists essentially of, or consists of) a homogeneous mixture throughout its core, the mixture comprising (or consisting essentially of, or consists of):
            40 wt-% to 50 wt-% of topiramate, based on the total weight of an uncoated particle core;
            45 wt-% to 55 wt-% of one or more filler(s), based on the total weight of an uncoated particle core; and
            3 wt-% to 7 wt-% of one or more binder(s), based on the total weight of an uncoated particle core;
        wherein the coating comprises (or consists essentially of, or consists of):
            55 wt-% to 65 wt-% of one or more release control agent(s), based on the total weight of the coating;
            20 wt-% to 25 wt-% of one or more pore former(s), based on the total weight of the coating; and
            10 wt-% to 20 wt-% of one or more plasticizer(s), based on the total weight of the coating;
        wherein the particles are coated in an amount sufficient to provide a weight gain of 8% to 14%.
4. The extended-release topiramate capsule of any of embodiments 1 through 3 wherein the particles are coated in an amount sufficient to provide a weight gain of 10% to 12%.
5. The extended-release topiramate capsule of any of embodiments 1 through 4 wherein the one or more filler(s) is selected from the group of microcrystalline cellulose, dibasic calcium phosphate, lactose, tribasic calcium phosphate, mannitol, and combinations thereof.
6. The extended-release topiramate capsule of embodiment 5 wherein the filler is microcrystalline cellulose.
7. The extended-release topiramate capsule of any of embodiments 1 through 6 wherein the one or more binder(s) is selected from the group of hydroxypropyl methylcellulose, methylcellulose, carboxymethylcellulose, sodium carboxymethylcellulose, hydroxypropyl cellulose, hydroxyethylcellulose, polyvinyl pyrrolidine, starch, natural gum, and combinations thereof
8. The extended-release topiramate capsule of embodiment 7 wherein the binder is hydroxypropyl methylcellulose.
9. The extended-release topiramate capsule of any of embodiments 1 through 8 wherein the one or more release controlling agent(s) is selected from the group of ethylcellulose, polyvinyl acetate, polyacrylate and polymethacrylate, copolymers thereof, and combinations thereof
10. The extended-release topiramate capsule of embodiment 9 wherein the release controlling agent is ethylcellulose.
11. The extended-release topiramate capsule of any of embodiments 1 through 10 wherein the one or more pore former(s) is selected from the group of hypromellose, hydroxypropyl cellulose, methylcellulose, hydroxyethylcellulose, carboxymethylcellulose, sodium carboxymethylcellulose, polyethylene glycol, guar gum, xanthan gum, sodium alginate, polyvinylpyrrolidone, crospovidone, sodium starch glycolate, croscarmellose sodium, starch, mannitol, glucose, sucrose, fructose, mannose, galactose, sorbitol, dextran, sodium chloride, potassium chloride, calcium chloride, and combinations thereof
12. The extended-release topiramate capsule of embodiment 11 wherein the pore former is hydroxypropyl methylcellulose.
13. The extended-release topiramate capsule of any of embodiments 1 through 12 wherein the one or more plasticizer(s) is selected from the group of diethyl phthalate, triethyl citrate, dibutyl sebacate, polyethylene glycol, triacetin, tributyl citrate, glycerol, propylene glycol, and combinations thereof
14. The extended-release topiramate capsule of embodiment 13 wherein the plasticizer is diethyl phthalate.
15. The extended-release topiramate capsule of any of embodiments 1 through 14 wherein each particle core further comprises one or more stabilizer(s).
16. The extended-release topiramate capsule of embodiment 15 wherein the one or more stabilizer(s) is selected from the group of calcium hydroxide, calcium carbonate, sodium bicarbonate, magnesium carbonate, and combinations thereof
17. The extended-release topiramate capsule of embodiment 15 or 16 wherein the one or more stabilizer(s) is present in an amount of 2 wt-% to 10 wt-%, based on the total weight of an uncoated particle core.
18. An extended-release topiramate capsule comprising (or consisting essentially of, or consisting of):
    a capsule shell comprising (or consisting essentially of, or consisting of) a single population of coated particles;
        wherein each coated particle comprises (or consists essentially of, or consists of) a core and a coating thereon;
        wherein each particle core comprises (or consists essentially of, or consists of) a homogeneous mixture throughout its core, the mixture comprising (or consisting essentially of, or consists of):
            40 wt-% to 50 wt-% of topiramate, based on the total weight of an uncoated particle core;
            45 wt-% to 55 wt-% of one or more filler(s), based on the total weight of an uncoated particle core;
                wherein the one or more filler(s) is selected from the group of microcrystalline cellulose, dibasic calcium phosphate, lactose, tribasic calcium phosphate, mannitol, and combinations thereof; and
            3 wt-% to 7 wt-% of one or more binder(s), based on the total weight of an uncoated particle core;
                wherein the one or more binder(s) is selected from the group of hydroxypropyl methylcellulose, methylcellulose, carboxymethylcellulose, sodium carboxymethylcellulose, hydroxypropyl cellulose, hydroxyethylcellulose, polyvinyl pyrrolidine, starch, natural gum, and combinations thereof;

wherein the coating comprises (or consists essentially of, or consists of):
- 55 wt-% to 65 wt-% of one or more release control agent(s), based on the total weight of the coating; wherein the one or more release controlling agent(s) is selected from the group of ethylcellulose, polyvinyl acetate, polyacrylate and polymethacrylate, copolymers thereof, and combinations thereof;
- 20 wt-% to 25 wt-% of one or more pore former(s), based on the total weight of the coating; wherein the one or more pore former(s) is selected from the group of hypromellose, hydroxypropyl cellulose, methylcellulose, hydroxyethylcellulose, carboxymethylcellulose, sodium carboxymethylcellulose, polyethylene glycol, guar gum, xanthan gum, sodium alginate, polyvinylpyrrolidone, crospovidone, sodium starch glycolate, croscarmellose sodium, starch, mannitol, glucose, sucrose, fructose, mannose, galactose, sorbitol, dextran, sodium chloride, potassium chloride, calcium chloride, and combinations thereof; and
- 10 wt-% to 20 wt-% of one or more plasticizer(s), based on the total weight of the coating; wherein the one or more plasticizer(s) is selected from the group of diethyl phthalate, triethyl citrate, dibutyl sebacate, polyethylene glycol, triacetin, tributyl citrate, glycerol, propylene glycol, and combinations thereof;

wherein the particles are coated in an amount sufficient to provide a weight gain of 8% to 14%.

19. An extended-release topiramate capsule comprising (or consisting essentially of, or consisting of):
a capsule shell comprising (or consisting essentially of, or consisting of) a single population of coated particles;
wherein each coated particle comprises (or consists essentially of, or consists of) a core and a coating thereon;
wherein each particle core comprises (or consists essentially of, or consists of) a homogeneous mixture throughout its core, the mixture comprising (or consisting essentially of, or consisting of):
- 40-50 wt-% of topiramate, based on the total weight of an uncoated particle core;
- 45-55 wt-% of microcrystalline cellulose, based on the total weight of an uncoated particle core; and
- 3-7 wt-% of hydroxypropyl methylcellulose, based on the total weight of an uncoated particle core;

wherein the coating comprises (or consists essentially of, or consists of):
- 55-65 wt-% of ethylcellulose, based on the total weight of the coating;
- 20-25 wt-% of hydroxypropyl methylcellulose, based on the total weight of the coating; and
- 10-20 wt-% of diethyl phthalate, based on the total weight of the coating;

wherein the particles are coated in an amount sufficient to provide a weight gain of 8% to 14%.

20. An extended-release topiramate capsule comprising (or consisting essentially of, or consisting of):
a capsule shell comprising (or consisting essentially of, or consisting of) a single population of coated particles;
wherein each coated particle comprises (or consists essentially of, or consists of) a core and a coating thereon;
wherein each particle core comprises (or consists essentially of, or consists of) a homogeneous mixture throughout its core, the mixture comprising (or consisting essentially of, or consisting of):
- 44-46 wt-% of topiramate, based on the total weight of an uncoated particle core;
- 48-52 wt-% of microcrystalline cellulose, based on the total weight of an uncoated particle core; and
- 4-6 wt-% of hydroxypropyl methylcellulose, based on the total weight of an uncoated particle core;

wherein the coating comprises (or consists essentially of, or consists of):
- 60-62 wt-% of ethylcellulose, based on the total weight of the coating;
- 22-24 wt-% of hydroxypropyl methylcellulose, based on the total weight of the coating; and
- 15-18 wt-% of diethyl phthalate, based on the total weight of the coating;

wherein the particles are coated in an amount sufficient to provide a weight gain of 10-12%.

21. The extended-release topiramate capsule of any of embodiments 1 through 20 which, when dosed to a healthy human subject once daily (e.g., in the morning or evening), achieves at steady-state, an $AUC_{0-24h}$, $C_{max}$, and $C_{min}$ in the subject's plasma that are within the 80% to 125% bioequivalence criteria compared to immediate-release topiramate dosed twice per day.

22. The extended-release topiramate capsule of any of embodiments 1 through 21 which, when dosed to a healthy human subject once daily in the morning, achieves at steady-state, a reduction of fluctuation index of at least 15% compared to immediate-release topiramate dosed twice per day.

23. The extended-release topiramate capsule of embodiment 22 which, when dosed to a healthy human subject once daily in the morning, achieves at steady-state, a reduction of fluctuation index of at least 20% compared to immediate-release topiramate dosed twice per day.

24. The extended-release topiramate capsule of embodiment 23 which, when dosed to a healthy human subject once daily in the morning, achieves at steady-state, a reduction of fluctuation index of at least 25% compared to immediate-release topiramate dosed twice per day.

25. The extended-release topiramate capsule of any of embodiments 1 through 24 which, when dosed to a healthy human subject once daily in the morning, achieves at steady-state, a $C_{min}$ in the subject's plasma that is higher than the $C_{min}$ compared to immediate-release topiramate dosed twice per day.

26. The extended-release topiramate capsule of any of embodiments 1 through 25 which, when given as a single-dose to a healthy human subject, achieves an $AUC_{0-inf}$ of 170 to 210 h·µg/mL within a 95% confidence interval, and a $C_{max}$ of 2 to 4 µg/mL within a 95% confidence interval.

27. The extended-release topiramate capsule of any of embodiments 1 through 26 which, when dosed once daily to a population of human patients suffering from epilepsy, achieves a reduction in incidence of at least one side effect compared to immediate-release topiramate dosed at the same total daily dose divided twice per day.

28. The extended-release topiramate capsule of any of embodiments 1 through 27 which is chemically stable for at least 12 months.

29. The extended-release topiramate capsule of embodiment 28 which is chemically stable for at least 24 months.

30. The extended-release topiramate capsule of embodiment 29 which is chemically stable for at least 24 months when stored in a sealed container with desiccant.

31. The extended-release topiramate capsule of embodiment 30 which is chemically stable for at least 36 months when stored in a sealed container with desiccant.
32. The extended-release topiramate capsule of any of embodiments 1 through 31 which is free of an immediate release component.
33. The extended-release topiramate capsule of any of embodiments 1 through 32 wherein the coated particles have a sphericity of at least 0.7.
34. The extended-release topiramate capsule of any of embodiments 1 through 33 wherein the coated particles have a particle size of at least 500 µm.
35. The extended-release topiramate capsule of any of embodiments 1 through 34 wherein the coated particles have a particle size of up to 1300 µm.
36. The extended-release topiramate capsule of any of embodiments 1 through 35 wherein the capsule shell comprises hydroxypropyl methylcellulose or gelatin.
37. The extended-release topiramate capsule of embodiment 36 wherein the capsule shell is a hydroxypropyl methylcellulose capsule.
38. A container comprising an extended-release topiramate capsule of any of embodiments 1 through 37 and desiccant.
39. The container of embodiment 38 wherein the ratio of weight of desiccant to weight of filled capsules is at least 0.01.
40. The container of embodiment 38 or 39 wherein the ratio of weight of desiccant to weight of filled capsules is up to 0.9.
41. The container of any of embodiments 38 through 40 wherein the desiccant is selected from silica gel, bentonite clay, molecular sieve, and combinations thereof.
42. A method of dosing a subject in need thereof, the method comprising administering an extended-release topiramate capsule of any of embodiments 1 through 37 once daily to the subject.
43. The method of embodiment 42 wherein the administering occurs once daily in the morning.
44. The method of embodiment 42 wherein the administering occurs once daily in the evening.
45. The method of any of embodiments 42 through 44 wherein the dosing is for the treatment of convulsions.
46. The method of any of embodiments 42 through 44 wherein the dosing is for the prophylactic treatment of a migraine.

EXAMPLES

Process and Formulations

1. High Shear Granulation: The core bead components listed in the table below are added to the high shear granulator and blended. After the pre-mix step, Purified Water is added to the high shear granulator and the mixture kneaded to create a wet granulation.
2. Extrusion: The wet granulation is then fed at a specified rate into a twin dome extruder equipped with dome dies having 0.8 mm pores to form an extrudate.
3. Spheronization: Portions of the extrudate from the extruder are weighed out and processed, for a specified time sufficient to form spherical particles (i.e., beads), in a spheronizer equipped with a 2×2 mm friction plate.
4. Drying: The wet spherical particles are dried in a fluid bed processor to a moisture content of not more than (NMT) 3.0% w/w, as determined by an in-process loss-on-drying analysis.
5. Sizing: The dried particles are sized using a 14-mesh and a 30-mesh sieve (Market Grade mesh screen). Material passing through the 14-mesh sieve, but retained on the 30-mesh sieve is taken into the subsequent coating step.
6. Coating: The dried, sized, uncoated beads are coated in a Würster fluidized bed processor to a desired coating weight gain using the coating composition listed in the table below.
7. Sizing: Following coating, the beads are sized using a 14-mesh and a 30-mesh sieve (Market Grade mesh screen). Material passing through the 14-mesh sieve, but retained on the 30-mesh sieve is taken into the subsequent encapsulation step.
8. Encapsulation: Using a suitable encapsulator, appropriate amounts of coated beads are filled into appropriate size capsules to yield the different strengths of the product. The encapsulated product is also run through a capsule polisher, metal detector, and weight checker.

| Formulation designation | A | B |
|---|---|---|
| Coating Weight Gain** | 12% w/w | 10% w/w |
| Core particle components (% w/w, based on weight of the core) | | |
| Topiramate | 45 | 45 |
| Microcrystalline Cellulose | 50 | 50 |
| Hypromellose 2910 | 5 | 5 |
| Coating components*** (% w/w, based on weight of the coating) | | |
| Ethylcellulose | 60.86 | 60.86 |
| Hypromellose 2910 | 22.56 | 22.56 |
| Diethyl Phthalate | 16.58 | 16.58 |
| Dehydrated Alcohol* | NA | NA |
| Purified Water* | NA | NA |

*Removed during processing.
**Weight gain is defined as the theoretical weight gain after coating of a population of uncoated particles, assuming 100% coating efficiency.
***The solids content (non-volatile components, i.e., ethylcellulose, hypromellose 2910 and diethyl phthalate) of the coating solution was 7.5% w/w for B and 6% w/w for A. The ratio of Dehydrated Alcohol to Purified Water is about 3.7:1 on a weight basis.

PK Results

In clinical studies, the extended-release topiramate capsules of Formulation A, when given as a single-dose to a healthy human subject, achieved an $AUC_{0\text{-}inf}$ of 173.9 to 200.1 h·µg/mL within a 95% confidence interval, and a $C_{max}$ of 2.64 to 3.16 µg/mL within a 95% confidence interval.

In clinical studies, the extended-release topiramate capsules of Formulation B, when given as a single-dose to a healthy human subject, achieved an $AUC_{0\text{-}inf}$ of 179.7 to 204.3 h·µg/mL within a 95% confidence interval, and a $C_{max}$ of 2.94 to 3.43 µg/mL within a 95% confidence interval.

Adverse Event Evaluation

In clinical studies, the extended-release topiramate capsules of the present disclosure, when dosed to patients with epilepsy (more specifically, as adjunctive treatment in patients with refractory partial onset seizure with or without generalization) once daily, achieved a reduction in incidence of at least one side effect compared to immediate-release topiramate dosed at the same total daily dose divided twice per day.

This comparison is based on the extended-release topiramate capsules of the present disclosure compared to placebo, and the immediate-release topiramate (TOPAMAX) compared to placebo. Each being compared to placebo (as opposed to each other), this evaluation demonstrated that the extended-release topiramate capsules of the present disclosure achieve a reduction in at least one side effect (e.g., somnolence, dizziness, ataxia, disturbance in attention, memory impairment, cognitive disorder, and psychomotor slowing).

Alcohol Dose Dumping

Capsules of the present disclosure, which included an ethanol-soluble particle coating, were evaluated in vitro for dose dumping in ethanol using a USP apparatus 1 (baskets) operating at 100 revolutions per minute (rpm) with a pH 1.2 HCl buffer containing 5 to 40% v/v (volume by volume) ethanol. There was no evidence of immediate release or unacceptable acceleration of release of the topiramate.

Sulfate/Sulfamate Method

Sulfate and Sulfamate degradation products were measured utilizing an ion chromatography (IC) method with ion suppression conductivity detection. The chromatographic system used an Alltech Novosep A-2, 250×4.0 mm, 5-μm particle size column maintained at 43° C. The flow rate of the 3.6 mM sodium carbonate mobile phase was 1.0 mL/min. A 7 mg/mL solution of topiramate in water containing 10% acetonitrile was prepared from particles (removed from a capsule of the present disclosure) using sonication and mixing to extract the sulfate and sulfamate degradation products. Particles within the capsules of the present disclosure demonstrated little or no decomposition after a given time period, such that no more than 2000 parts per million (ppm) each of sulfate or sulfamate degradation products were produced.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An extended-release topiramate capsule comprising:
   a capsule shell comprising a single population of coated particles;
      wherein each coated particle comprises a core and a coating thereon;
      wherein each particle core comprises a homogeneous mixture throughout its core,
   the mixture comprising:
      40 wt-% to 50 wt-% of topiramate, based on the total weight of an uncoated particle core;
      45 wt-% to 55 wt-% of one or more filler(s), based on the total weight of an uncoated particle core; and
      3 wt-% to 7 wt-% of one or more binder(s), based on the total weight of an uncoated particle core;
   wherein the coating comprises:
      55 wt-% to 65 wt-% of one or more release control agent(s), based on the total weight of the coating;
      20 wt-% to 25 wt-% of one or more pore former(s), based on the total weight of the coating; and
      10 wt-% to 20 wt-% of one or more plasticizer(s), based on the total weight of the coating;
   wherein the particles are coated in an amount sufficient to provide a weight gain of 8% to 14%.

2. The extended-release topiramate capsule of claim 1 which, when dosed to a healthy human subject once daily, achieves at steady-state, an $AUC_{0-24h}$, $C_{max}$, and $C_{min}$ in the subject's plasma that are within the 80% to 125% bioequivalence criteria compared to immediate-release topiramate dosed twice per day.

3. The extended-release topiramate capsule of claim 1 which, when dosed to a healthy human subject once daily in the morning, achieves at steady-state, a reduction of fluctuation index of at least 15% compared to immediate-release topiramate dosed twice per day.

4. The extended-release topiramate capsule of claim 1 which, when dosed to a healthy human subject once daily in the morning, achieves at steady-state, a $C_{min}$ in the subject's plasma that is higher than the $C_{min}$ compared to immediate-release topiramate dosed twice per day.

5. The extended-release topiramate capsule of claim 1 which, when a single-dose is given to a healthy human subject, achieves an $AUC_{0-inf}$ of 170 to 210 h·μg/mL within a 95% confidence interval, and a $C_{max}$ of 2 to 4 μg/mL within a 95% confidence interval.

6. The extended-release topiramate capsule of claim 1 which, when dosed once daily to a population of human patients suffering from epilepsy, achieves a reduction in incidence of at least one side effect compared to immediate-release topiramate dosed at the same total daily dose divided twice per day.

7. The extended-release topiramate capsule of claim 1 wherein the particles are coated in an amount sufficient to provide a weight gain of 10% to 12%.

8. The extended-release topiramate capsule of claim 1 which is chemically stable for at least 12 months.

9. The extended-release topiramate capsule of claim 8 which is chemically stable for at least 24 months when stored in a sealed container with desiccant.

10. The extended-release topiramate capsule of claim 1 wherein the capsule shell is a hydroxypropyl methylcellulose capsule.

11. The extended-release topiramate capsule of claim 1 which is free of an immediate-release component.

12. The extended-release topiramate capsule of claim 1 wherein the one or more filler(s) is selected from the group of microcrystalline cellulose, dibasic calcium phosphate, lactose, tribasic calcium phosphate, mannitol, and combinations thereof.

13. The extended-release topiramate capsule of claim 12 wherein the filler is microcrystalline cellulose.

14. The extended-release topiramate capsule of claim 1 wherein the one or more binder(s) is selected from the group of hydroxypropyl methylcellulose, methylcellulose, carboxymethylcellulose, sodium carboxymethylcellulose, hydroxypropyl cellulose, hydroxyethylcellulose, polyvinyl pyrrolidine, starch, natural gum, and combinations thereof.

15. The extended-release topiramate capsule of claim 14 wherein the binder is hydroxypropyl methylcellulose.

16. The extended-release topiramate capsule of claim 1 wherein the one or more release controlling agent(s) is selected from the group of ethylcellulose, polyvinyl acetate, polyacrylate and polymethacrylate, copolymers thereof, and combinations thereof.

17. The extended-release topiramate capsule of claim 16 wherein the release controlling agent is ethylcellulose.

18. The extended-release topiramate capsule of claim 1 wherein the one or more pore former(s) is selected from the group of hypromellose, hydroxypropyl cellulose, methylcellulose, hydroxyethylcellulose, carboxymethylcellulose, sodium carboxymethylcellulose, polyethylene glycol, guar gum, xanthan gum, sodium alginate, polyvinylpyrrolidone, crospovidone, sodium starch glycolate, croscarmellose sodium, starch, mannitol, glucose, sucrose, fructose, mannose, galactose, sorbitol, dextran, sodium chloride, potassium chloride, calcium chloride, and combinations thereof.

19. The extended-release topiramate capsule of claim 18 wherein the pore former is hydroxypropyl methylcellulose.

20. The extended-release topiramate capsule of claim 1 wherein the one or more plasticizer(s) is selected from the group of diethyl phthalate, triethyl citrate, dibutyl sebacate, polyethylene glycol, triacetin, tributyl citrate, glycerol, propylene glycol, and combinations thereof.

21. The extended-release topiramate capsule of claim 20 wherein the plasticizer is diethyl phthalate.

22. The extended-release topiramate capsule of claim 1 wherein each particle core further comprises one or more stabilizer(s) selected from the group of calcium hydroxide, calcium carbonate, sodium bicarbonate, magnesium carbonate, and combinations thereof.

23. An extended-release topiramate capsule comprising:
   a capsule shell comprising a single population of coated particles;
      wherein each coated particle comprises a core and a coating thereon;
      wherein each particle core comprises a homogeneous mixture throughout its core,
   the mixture comprising:
      40 wt-% to 50 wt-% of topiramate, based on the total weight of an uncoated particle core;
      45 wt-% to 55 wt-% of one or more filler(s), based on the total weight of an uncoated particle core; wherein the one or more filler(s) is selected from the group of microcrystalline cellulose, dibasic calcium phosphate, lactose, tribasic calcium phosphate, mannitol, and combinations thereof; and
      3 wt-% to 7 wt-% of one or more binder(s), based on the total weight of an uncoated particle core; wherein the one or more binder(s) is selected from the group of hydroxypropyl methylcellulose, methylcellulose, carboxymethylcellulose, sodium carboxymethylcellulose, hydroxypropyl cellulose, hydroxyethylcellulose, polyvinyl pyrrolidine, starch, natural gum, and combinations thereof;
   wherein the coating comprises:
      55 wt-% to 65 wt-% of one or more release control agent(s), based on the total weight of the coating; wherein the one or more release controlling agent(s) is selected from the group of ethylcellulose, polyvinyl acetate, polyacrylate and polymethacrylate, copolymers thereof, and combinations thereof;
      20 wt-% to 25 wt-% of one or more pore former(s), based on the total weight of the coating; wherein the one or more pore former(s) is selected from the group of hypromellose, hydroxypropyl cellulose, methylcellulose, hydroxyethylcellulose, carboxymethylcellulose, sodium carboxymethylcellulose, polyethylene glycol, guar gum, xanthan gum, sodium alginate, polyvinylpyrrolidone, crospovidone, sodium starch glycolate, croscarmellose sodium, starch, mannitol, glucose, sucrose, fructose, mannose, galactose, sorbitol, dextran, sodium chloride, potassium chloride, calcium chloride, and combinations thereof; and
      10 wt-% to 20 wt-% of one or more plasticizer(s), based on the total weight of the coating; wherein the one or more plasticizer(s) is selected from the group of diethyl phthalate, triethyl citrate, dibutyl sebacate, polyethylene glycol, triacetin, tributyl citrate, glycerol, propylene glycol, and combinations thereof;
   wherein the particles are coated in an amount sufficient to provide a weight gain of 8% to 14%.

24. The extended-release topiramate capsule of claim 23 which, when dosed to a healthy human subject once daily, achieves at steady-state, an $AUC_{0-24h}$, $C_{max}$, and $C_{min}$ in the subject's plasma that are within the 80% to 125% bioequivalence criteria compared to immediate-release topiramate dosed twice per day.

25. The extended-release topiramate capsule of claim 23 which, when dosed to a healthy human subject once daily in the morning, achieves at steady-state a reduction of fluctuation index of at least 15% compared to immediate-release topiramate dosed twice per day.

26. The extended-release topiramate capsule of claim 23 which, when dosed to a healthy human subject once daily in the morning, achieves at steady-state a $C_{min}$ in the subject's plasma that is higher than the $C_{min}$ compared to immediate-release topiramate dosed twice per day.

27. The extended-release topiramate capsule of claim 23 which, when given as a single-dose to a healthy human subject, achieves an $AUC_{0-inf}$ of 170 to 210 h·µg/mL within a 95% confidence interval, and a $C_{max}$ of 2 to 4 µg/mL within a 95% confidence interval.

28. The extended-release topiramate capsule of claim 23 which, when dosed once daily to a population of human patients suffering from epilepsy, achieves a reduction in incidence of at least one side effect compared to immediate-release topiramate dosed at the same total daily dose divided twice per day.

29. An extended-release topiramate capsule comprising:
   a capsule shell comprising a single population of coated particles;
      wherein each coated particle comprises a core and a coating thereon;
      wherein each particle core comprises a homogeneous mixture throughout its core,
   the mixture comprising:
      40-50 wt-% of topiramate, based on the total weight of an uncoated particle core;
      45-55 wt-% of microcrystalline cellulose, based on the total weight of an uncoated particle core; and
      3-7 wt-% of hydroxypropyl methylcellulose, based on the total weight of an uncoated particle core;
   wherein the coating comprises:
      55-65 wt-% of ethylcellulose, based on the total weight of the coating;
      20-25 wt-% of hydroxypropyl methylcellulose, based on the total weight of the coating; and
      10-20 wt-% of diethyl phthalate, based on the total weight of the coating;
   wherein the particles are coated in an amount sufficient to provide a weight gain of 8% to 14%.

30. An extended-release topiramate capsule comprising:
   a capsule shell comprising a single population of coated particles;
      wherein each coated particle comprises a core and a coating thereon;
      wherein each particle core comprises a homogeneous mixture throughout its core,
   the mixture comprising:
      44-46 wt-% of topiramate, based on the total weight of an uncoated particle core;
      48-52 wt-% of microcrystalline cellulose, based on the total weight of an uncoated particle core; and
      4-6 wt-% of hydroxypropyl methylcellulose, based on the total weight of an uncoated particle core;
   wherein the coating comprises:
      60-62 wt-% of ethylcellulose, based on the total weight of the coating;
      22-24 wt-% of hydroxypropyl methylcellulose, based on the total weight of the coating; and 15-18 wt-% of diethyl phthalate, based on the total weight of the coating;

wherein the particles are coated in an amount sufficient to provide a weight gain of 10-12%.

* * * * *

UNITED STATES PATENT AND TRADEMARK OFFICE
CERTIFICATE OF CORRECTION

| | | |
|---|---|---|
| PATENT NO. | : 8,652,527 B1 | Page 1 of 1 |
| APPLICATION NO. | : 13/847042 | |
| DATED | : February 18, 2014 | |
| INVENTOR(S) | : Sarah Michelle Betterman et al. | |

It is certified that error appears in the above-identified patent and that said Letters Patent is hereby corrected as shown below:

On the Title Page:

Item (71) Applicants
Delete "Jaidev Srinvas Tantry" and insert --Jaidev Srinivas Tantry--

Item (72) Inventors
Delete "Jaidev Srinvas Tantry" and insert --Jaidev Srinivas Tantry--

In the Specifications:

Column 2, Line 28
Insert a --.-- before "Thus"

Column 9, line 67
Insert a --.-- after "thereof"

Column 10, line 7
Insert a --.-- after "thereof"

Column 10, line 20
Insert a --.-- after "thereof"

Column 10, line 29
Insert a --.-- after "thereof"

Column 10, line 39
Insert a --.-- after "thereof"

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,652,527 B1 | Page 1 of 1 |
| APPLICATION NO. | : 13/847042 | |
| DATED | : February 18, 2014 | |
| INVENTOR(S) | : Sarah Michelle Betterman, Jaidev Srinivas Tantry and Laura Marie Patrick | |

It is certified that error appears in the above-identified patent and that said Letters Patent is hereby corrected as shown below:

On the Title Page

Under (71) Applicants:

Delete:

"Sarah Michelle Betterman, Champlin, MN (US); Jaidev Srinivas Tantry, Maple Grove, MN (US); Laura Marie Patrick, Eden Prairie, MN (US)"

and insert:

-- Upsher-Smith Laboratories, Inc., Maple Grove, MN (US) --

Signed and Sealed this
Thirteenth Day of January, 2015

Michelle K. Lee
*Deputy Director of the United States Patent and Trademark Office*